United States Patent
Clarke et al.

(10) Patent No.: US 9,329,170 B2
(45) Date of Patent: May 3, 2016

(54) SINGLE CELL GENE EXPRESSION FOR DIAGNOSIS, PROGNOSIS AND IDENTIFICATION OF DRUG TARGETS

(75) Inventors: Michael F. Clarke, Palo Alto, CA (US); Stephen R. Quake, Stanford, CA (US); Piero D. Dalerba, Palo Alto, CA (US); Huiping Liu, Chicago, IL (US); Anne Leyrat, San Carlos, CA (US); Tomer Kalisky, Palo Alto, CA (US); Maximilian Diehn, Stanford, CA (US); Jianbin Wang, Stanford, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 718 days.

(21) Appl. No.: 12/657,457

(22) Filed: Jan. 20, 2010

(65) Prior Publication Data

US 2010/0255471 A1    Oct. 7, 2010

Related U.S. Application Data

(60) Provisional application No. 61/205,485, filed on Jan. 20, 2009.

(51) Int. Cl.
*G01N 33/50* (2006.01)
*C12Q 1/68* (2006.01)

(52) U.S. Cl.
CPC .......... *G01N 33/5023* (2013.01); *C12Q 1/6886* (2013.01); *C12Q 2600/106* (2013.01); *C12Q 2600/112* (2013.01); *C12Q 2600/136* (2013.01); *C12Q 2600/178* (2013.01); *G01N 2800/52* (2013.01)

(58) Field of Classification Search
None
See application file for complete search history.

(56) References Cited

U.S. PATENT DOCUMENTS

| | | |
|---|---|---|
| 5,750,341 A | 5/1998 | Macevicz |
| 5,969,119 A | 10/1999 | Macevicz |
| 6,228,575 B1 | 5/2001 | Gingeras et al. |
| 6,306,597 B1 | 10/2001 | Macevicz |
| 6,308,170 B1 | 10/2001 | Balaban |
| 7,170,050 B2 | 1/2007 | Turner et al. |
| 7,211,390 B2 | 5/2007 | Rothberg et al. |
| 7,244,559 B2 | 7/2007 | Rothberg et al. |
| 7,244,567 B2 | 7/2007 | Chen et al. |
| 7,264,929 B2 | 9/2007 | Rothberg et al. |
| 7,276,720 B2 | 10/2007 | Ulmer |
| 7,302,146 B2 | 11/2007 | Turner et al. |
| 7,313,308 B2 | 12/2007 | Turner et al. |
| 7,315,019 B2 | 1/2008 | Turner et al. |
| 7,323,305 B2 | 1/2008 | Leamon et al. |
| 7,335,762 B2 | 2/2008 | Rothberg et al. |
| 7,405,281 B2 | 7/2008 | Xu et al. |
| 7,462,452 B2 | 12/2008 | Williams et al. |
| 7,462,468 B1 | 12/2008 | Williams et al. |
| 7,476,503 B2 | 1/2009 | Turner et al. |
| 7,476,504 B2 | 1/2009 | Turner |
| 7,491,498 B2 | 2/2009 | Lapidus et al. |
| 7,501,245 B2 | 3/2009 | Quake et al. |
| 2005/0059147 A1 | 3/2005 | Seshi |
| 2006/0024678 A1 | 2/2006 | Buzby |
| 2006/0024711 A1 | 2/2006 | Lapidus et al. |
| 2006/0286566 A1 | 12/2006 | Lapidus et al. |
| 2008/0087826 A1 | 4/2008 | Harris et al. |
| 2008/0103058 A1 | 5/2008 | Siddiqi |
| 2008/0206764 A1 | 8/2008 | Williams et al. |
| 2008/0213770 A1 | 9/2008 | Williams et al. |
| 2009/0024331 A1 | 1/2009 | Tomaney et al. |
| 2009/0029385 A1 | 1/2009 | Christians |
| 2009/0061439 A1 | 3/2009 | Buzby |
| 2009/0068655 A1 | 3/2009 | Williams |

FOREIGN PATENT DOCUMENTS

| | | | |
|---|---|---|---|
| CN | 102333891 A | 1/2012 | |
| JP | 2012515533 A | 7/2012 | |
| KR | 102011013834 | 12/2011 | |
| WO | WO 2007/114896 A2 * | 10/2007 | ........... C12Q 1/6886 |
| WO | WO-2010/085498 A1 | 7/2010 | |

OTHER PUBLICATIONS

Wheeler et al "Microfluidic Device for Single-Cell Analysis" (Anal Chem 2003: vol. 75 pp. 3581-3586).*
Lui et al in "The Prognostic Role of a Gene Signature from Tumorigenic Breast-Cancer Cells" (New England Journal of Medicine, Jan. 2007, vol. 356, No. 3, Supplementary Appendix pp. 1-11 and 11 additional pages of Tables and Figures).*
Kurimoto et al in "An improved single-cell cDNA amplification method for efficient high-density oligonucleotide microarray analysis" (NAR, published online Mar. 17, 2006: vol. 34, No. 5: pp. 1-17).*
Wheeler et al "Microfluidic Device for Single-Cell Analysis" (Anal Chem 2003: vol. 75 pp. 3581-3586;.*
Bontoux et al in "Integrating whole transcriptome assays on a lab-on-a-chip for single cell gene profiling" (Lab Chip, 2008: vol. 8, pp. 443-450; published Jan. 31, 2008; IDS submission filed on Nov. 30, 2012).*
Alessandro; et al., "Proteomic Approaches in Colon Cancer: Promising Tools for New Cancer Markers and Drug Target Discovery", Clinical Colorectal Cancer (2005), 4(6):396-402.

(Continued)

*Primary Examiner* — Catherine S Hibbert
(74) *Attorney, Agent, or Firm* — Schwegman Lundberg & Woessner, P.A.

(57) ABSTRACT

Methods are provided for diagnosis and prognosis of disease by analyzing expression of a set of genes obtained from single cell analysis. Classification allows optimization of treatment, and determination of whether on whether to proceed with a specific therapy, and how to optimize dose, choice of treatment, and the like. Single cell analysis also provides for the identification and development of therapies which target mutations and/or pathways in disease-state cells.

11 Claims, 12 Drawing Sheets
(11 of 12 Drawing Sheet(s) Filed in Color)

(56) References Cited

OTHER PUBLICATIONS

Fu; et al., "A microfabricated Fluorescence-activated cell sorter", Nature Biotechnology (1999) 17:1109-11.
Fu; et al., "An Integrated Microfabricated Cell Sorter", Analytical Chemistry (2002), 74(11):2451-57.
Graudens; et al., "Deciphering cellular states of innate tumor drug responses", Genome Biology (2006), 7(3):R19-R19.21.
Liu; et al., "The Prognostic Role of a Gene Signature from Tumorigenic Breast-Cancer Cells", The New England Journal of Medicine, 356(3):217-26.
Marcus; et al., "Microfluidic Single-Cell mRNA Isolation and Analysis", Analytical Chemistry (2006), 78(9):3084-89.
Margulies; et al., "Genome Sequencing in microfabricated high-density picolitre reactors", Nature (2005), 437:376-80.
Schaner; et al., "Gene Expression Patterns in Ovarian Carcinomas", Molecular Biology of the Cell (2003), 14:4376-86.
Tibshirani; et al., "Diagnosis of multiple cancer types by shrunken centroids of gene expression", PNAS (2002), 99 (10):6567-6572.
Tokimitsu; et al., "Single Lymphocyte Analysis with a Microwell Array Chip", Cytometry Part A (2007), 71A: 1003-1010.
Tusher; et al., "Significance analysis of microarrays applied to the ionizing radiation response", PNAS (2001), 98 (9):5116-5121.
Yamamura; et al., "Single-Cell Microarray for Analyzing Cellular Response", Analytical Chemistry (2005), 77 (24):8050-8056.
"International Application Serial No. PCT/US2010/021525, International Preliminary Report on Patentability mailed Aug. 4, 2011", 10 pgs.
"International Application Serial No. PCT/US2010/021525, International Search Report Mar. 17, 2010", 2 pgs.
"International Application Serial No. PCT/US2010/21525, Written Opinion mailed Mar. 17, 2010", 8 pgs.
Alessandro, R., et al., "Proteomic Approaches in Colon Cancer: Promising Tools for New Cancer Markers and Drug Target Discovery.", Clin Colorectal Cancer, 4(6), (Mar. 2005), 396-402.
Graudens, E., et al., "Deciphering cellular states of innate tumor drug responses.", Genome Biology, 7(3), R19.3-R19.4, R19.9, R19.14-R19.17, (Mar. 15, 2006), R19.
Marcus, J. S, et al., "Microfluidic single-cell mRNA isolation and analysis", Anal Chem., 78(9), Retrieved on Mar. 5 2010]. Retrieved from the Internet: <URL: http://thebigone.stanford.edu/loundry/services/PredesignedChipsisingle3eILanalchem06.pdf> Entire document, esp: abstract, p. DF, Fig. 1, Fig. 2, Fig. 3, Fig. 4., (May 1, 2006), 3084-9.
Schaner, M. E, et al., "Gene expression patterns in ovarian carcinomas", Mol Biol Cell., 14(11), (Nov. 2003), 4376-86.
"European Application Serial No. 10733816.2, Extended Search Report mailed Sep. 3, 2012", 9 pgs.
"European Application Serial No. 10733816.2, Office Action Response filed Mar. 12, 2012", 10 pgs.
Bontoux, N, et al., "Integrating whole transcriptome assays on a lab-on-a-chip for single cell gene profiling", Lab on a Chip, vol. 8 No. 3, (Jan. 1, 2008), 443.
Fitzpatrick, Ethan, et al., "Microfluidic Techniques for Single-Cell Protein Expression Analysis", Clinical Chemistry, vol. 52 No. 6, (Mar. 30, 2006), 1080-1088.
"Chinese Application Serial No. 201080009805.2, Office Action mailed Mar. 29, 2013", w/English translation, 7 pgs.
"European Application Serial No. 10733816.2, Examination Notification Art. 94(3) mailed Apr. 17, 2013", 5 pgs.
"European Application Serial No. 10733816.2, Response filed Mar. 15, 2013 to Extended European Search Report mailed Sep. 3, 2012", 8 pgs.
"European Application Serial No. 10733816.2, Response filed Aug. 13, 2013 to Examination Notification Art. 94(3) mailed Apr. 17, 2013", 17 pgs.
European Application Serial No. 10733816.2 Response filed Apr. 8, 2015 to Office Action mailed Oct. 9, 2014, 6 pgs.
Singaporean Application Serial No. 201105213-1, Search Report and Written Opinion mailed Nov. 4, 2013, 19 pgs.
Chen, Yan, et al., "Microfluidic devices for high-throughput gene expression profiling of single hESC-derived neural stem cells.", Methods in Molecular Biology, 438, (2008), 293-303.
Zhong, J. F., et al., "A microfluidic processor for gene expression profiling of single human embryonic stem cells", Lab on a Chip, 8(1), (2008), 68-74.
Zhong, J. F., et al., "Microfluidic devices for investigating stem cell gene regulation via single-cell analysis", Current Medicinal Chemistry, 15(28), (2008), 2897-2900.

\* cited by examiner

FIGURE 1
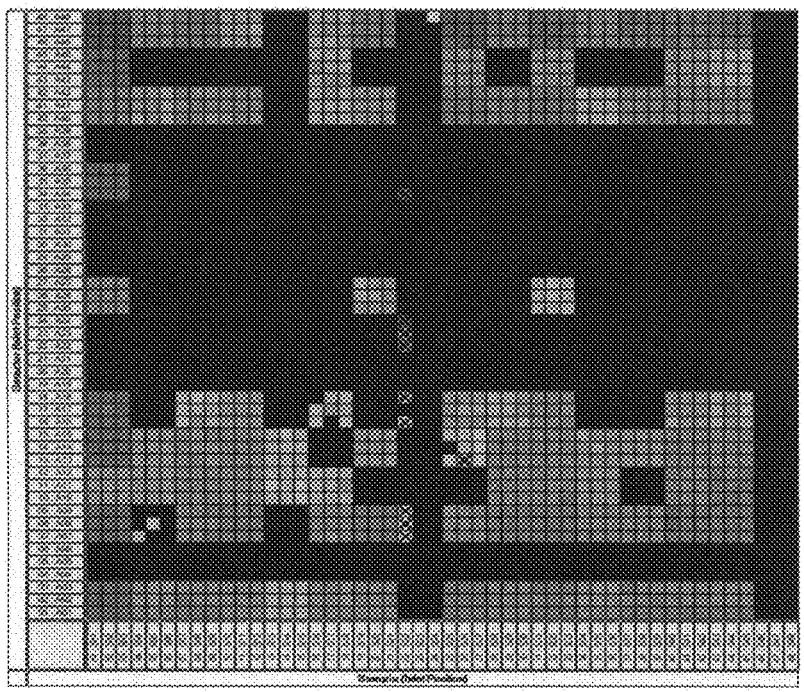
27 replicates
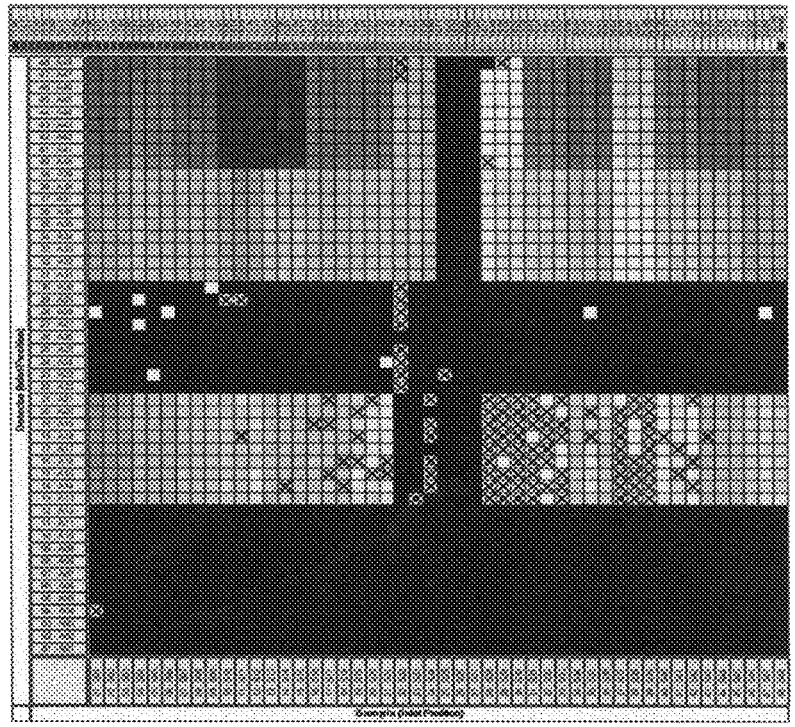
9 replicates

FIGURE 4

| | T3 P5 TG | T3 P5 NTG | T3 p5 TG-NTG | COH p1 TG | COH p1 NTG | COH p1 TG NTG | LP P2 TG | LP P2 NTG | LP P2 TG-NTG | MM P3 TG | MM P3 NTG | MM p0 TG NTG | MM P3 TG 0017 | MM P3 Lung IG | MM p0 Lung-Primary |
|---|---|---|---|---|---|---|---|---|---|---|---|---|---|---|---|
| | ER+ | ER+ | ER+ | ER-PR+ | ER-PR+ | ER- | ER-PR+ | ER-PR+ | ER- | ER- | ER- | ER- | ER- | ER- | ER-PR+ |
| m107 | 23.1 | 24.5 | | 25.8 | 25.2 | | 24.0 | 25.9 | | 25.6 | 26.1 | | 24.3 | 25.8 | |
| m10a | 21.3 | 20.4 | | 24.0 | 25.2 | | 27.6 | 40.0 | | 40.0 | 40.0 | 0.0 | 40.0 | 29.1 | |
| m10b | 20.4 | 18.4 | | 22.8 | 25.0 | | 21.9 | 24.0 | | 21.5 | 21.6 | | 25.4 | 23.2 | |
| m125b | 20.6 | 20.5 | | 24.4 | 25.9 | | 21.7 | 24.6 | | 20.9 | 21.7 | | 24.4 | 22.5 | |
| m128 | 29.7 | 28.8 | | 32.6 | 33.6 | | 28.7 | 32.2 | | 32.1 | 32.0 | | 32.8 | 28.8 | |
| m130a | 28.2 | 31.4 | | 27.8 | 29.6 | | 25.4 | 29.3 | | 29.7 | 28.8 | | 31.0 | 29.5 | |
| m130b | 25.9 | 28.8 | | 28.7 | 31.0 | | 25.1 | 30.8 | | 27.9 | 29.4 | | 40.0 | 32.7 | |
| m134 | 25.8 | 40.0 | | 40.0 | 40.0 | | 40.0 | 40.0 | | 40.0 | 40.0 | 0.0 | 40.0 | 40.0 | |
| m141 | 24.3 | 23.1 | | 23.7 | 25.7 | | 24.7 | 28.2 | | 22.7 | 22.8 | | 25.5 | 24.1 | |
| m146a | 28.2 | 26.8 | | 24.8 | 27.0 | | 21.0 | 22.7 | | 21.9 | 22.1 | | 27.0 | 25.2 | |
| m155 | 30.0 | 36.9 | | 30.4 | 40.0 | | 28.1 | 40.0 | | 30.7 | 31.0 | | 40.0 | 32.8 | |
| m182 | 25.2 | 24.2 | | 23.9 | 25.7 | | 25.7 | 28.8 | | 26.4 | 26.0 | | 28.2 | 28.0 | |
| m183 | 24.4 | 22.4 | | 24.1 | 27.4 | | 25.7 | 40.0 | | 27.7 | 26.7 | | 40.0 | 40.0 | |
| m197 | 24.1 | 23.1 | | 22.7 | 24.4 | | 23.1 | 25.3 | | 22.8 | 23.3 | | 27.6 | 24.3 | |
| m19a | 25.7 | 30.9 | | 28.7 | 40.0 | | 24.3 | 27.4 | | 40.0 | 39.9 | | 30.1 | 40.0 | |
| m200a | 26.0 | 24.0 | | 22.9 | 25.0 | | 25.2 | 27.1 | | 22.9 | 23.6 | | 26.2 | 25.0 | |
| m200b | 22.8 | 21.8 | | 20.5 | 22.8 | | 22.6 | 24.9 | | 21.0 | 21.9 | | 25.1 | 23.0 | |
| m200c | 18.5 | 17.0 | | 18.9 | 20.4 | | 21.4 | 21.4 | | 16.9 | 17.3 | | 21.2 | 18.8 | |
| m210 | 18.8 | 17.7 | | 20.1 | 21.2 | | 18.3 | 20.8 | | 20.1 | 20.4 | | 31.1 | 29.5 | |
| m222 | 19.2 | 25.3 | | 17.7 | 18.9 | | 17.9 | 21.9 | | 21.4 | 20.9 | | 25.8 | 21.1 | |
| m29a-3p | 22.2 | 20.8 | | 21.0 | 22.9 | | 22.3 | 25.5 | | 22.1 | 22.8 | | 25.6 | 23.6 | |
| m30b | 20.8 | 19.7 | | 20.3 | 21.6 | | 21.1 | 22.7 | | 21.0 | 21.7 | | 24.1 | 22.8 | |
| m320 | 21.5 | 20.0 | | 22.1 | 24.2 | | 21.2 | 40.0 | | 19.7 | 20.7 | | 40.0 | 21.9 | |
| m339 | 20.7 | 20.1 | | 20.7 | 22.3 | | 20.7 | 22.9 | | 20.2 | 20.4 | | 40.0 | 21.6 | |
| m34c | 27.2 | 26.2 | | 26.4 | 26.7 | | 27.7 | 26.4 | | 27.3 | 26.9 | | 26.8 | 26.8 | |
| m423 | 20.6 | 19.7 | | 22.0 | 24.8 | | 22.3 | 31.8 | | 23.5 | 23.8 | | 40.0 | 27.1 | |
| m429 | 40.0 | 30.4 | | 30.1 | 40.0 | | 31.2 | 40.0 | | 31.4 | 32.8 | | 33.5 | 30.6 | |
| m490 | 40.0 | 26.8 | | 40.0 | 40.0 | | 40.0 | 40.0 | | 40.0 | 29.6 | | 40.0 | 40.0 | |
| m93 | 21.3 | 20.3 | | 24.4 | 30.3 | | 20.8 | 27.7 | | 27.9 | 25.1 | | 26.6 | 30.0 | |
| m96 | 26.5 | 25.8 | | 25.8 | 27.4 | | 28.0 | 40.0 | | 27.9 | 28.7 | 0.0 | 40.0 | 26.6 | |
| NR3 | 18.5 | 17.9 | | 17.0 | 17.9 | | 20.4 | 22.4 | | 20.4 | 20.7 | 0.0 | 22.8 | 19.9 | |
| NR6 | 19.9 | 19.6 | | 19.9 | 21.1 | | 21.4 | 24.7 | | 20.0 | 20.6 | 0.0 | 24.0 | 20.8 | |

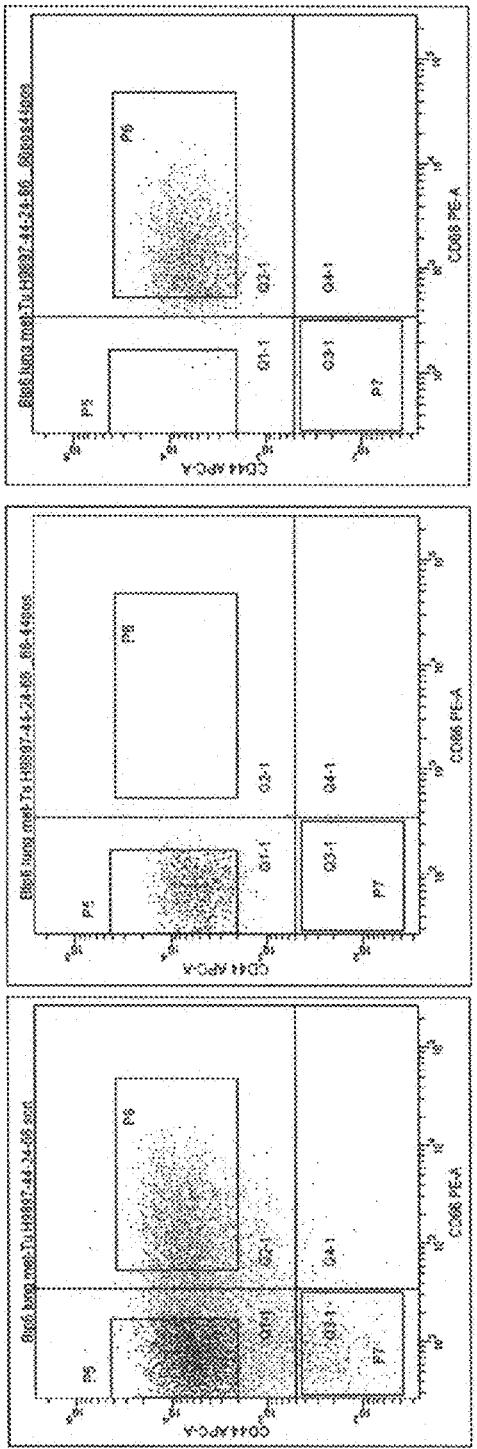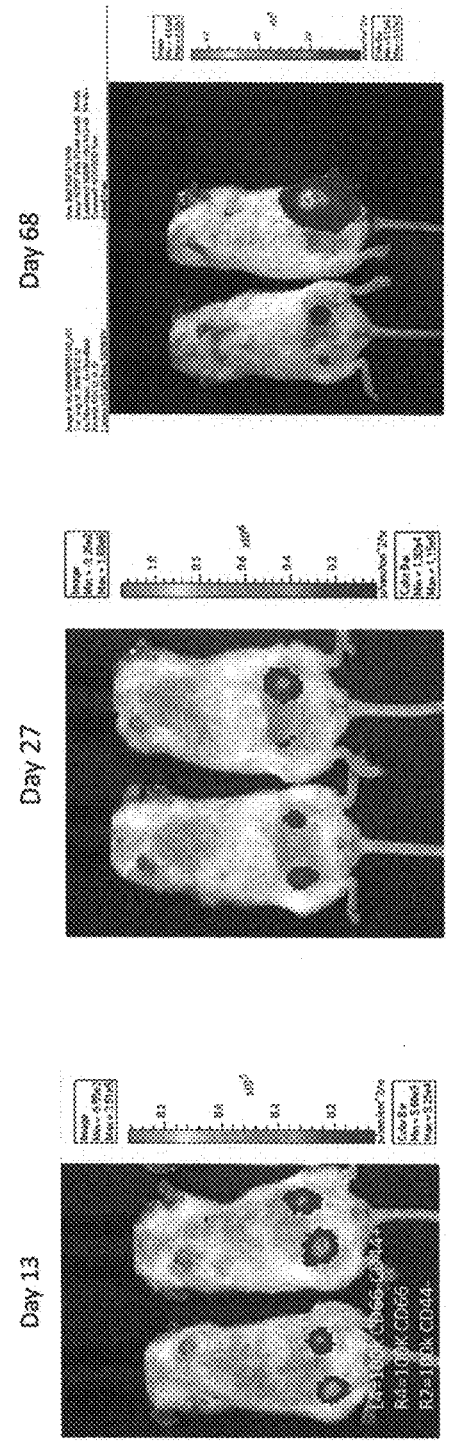
FIGURE 5D

SINGLE CELL GENE EXPRESSION FOR DIAGNOSIS, PROGNOSIS AND IDENTIFICATION OF DRUG TARGETS

CROSS-REFERENCE

This application claims the benefit of U.S. Provisional Application No. 61/205,485, filed Jan. 20, 2009, which application is incorporated herein by reference.

GOVERNMENT RIGHTS

This invention was made with Government support under contracts CA126524, OD000251, and CA104987 awarded by the National Cancer Institutes of Health. The Government has certain rights in this invention.

BACKGROUND OF THE INVENTION

In recent years, analysis of gene expression patterns has provided a way to improve the diagnosis and risk stratification of many diseases. For example, unsupervised analysis of global gene expression patterns has identified molecularly distinct subtypes of cancer, distinguished by extensive differences in gene expression, in diseases that were considered homogeneous based on classical diagnostic methods. Such molecular subtypes are often associated with different clinical outcomes. Global gene expression pattern can also be examined for features that correlate with clinical behavior to create prognostic signatures.

Cancer, like many diseases, is frequently not the result of a single, well-defined cause, but rather can be viewed as several diseases, each caused by different aberrations in informational pathways, which ultimately result in apparently similar pathologic phenotypes. Identification of polynucleotides that are differentially expressed in cancerous, pre-cancerous, or low metastatic potential cells relative to normal cells of the same tissue type can provide the basis for diagnostic tools, facilitates drug discovery by providing for targets for candidate agents, and further serves to identify therapeutic targets for cancer therapies that are more tailored for the type of cancer to be treated.

Identification of differentially expressed gene products also furthers the understanding of the progression and nature of complex diseases, and is key to identifying the genetic factors that are responsible for the phenotypes associated with development of, for example, the metastatic or inflammatory phenotypes. Identification of gene products that are differentially expressed at various stages, and in various types of cells, can both provide for early diagnostic tests, and further serve as therapeutic targets. Additionally, the product of a differentially expressed gene can be the basis for screening assays to identify chemotherapeutic agents that modulate its activity (e.g. its expression, biological activity, and the like).

Early disease diagnosis is of central importance to halting disease progression, and reducing morbidity. Analysis of a patient samples to identify gene expression patterns provides the basis for more specific, rational disease therapy that may result in diminished adverse side effects relative to conventional therapies. Furthermore, confirmation that a lesion poses less risk to the patient (e.g., that a tumor is benign) can avoid unnecessary therapies. In short, identification of gene expression patterns in disease-associated cells can provide the basis of therapeutics, diagnostics, prognostics, therametrics, and the like.

As another example, infectious diseases cause damage to tissues and organs that lead to the morbidity and mortality of a particular organism. In the case of influenza A infections, the most frequent cause of hospitalization and death is infection of the lung tissue. However, the precise cells that are infected by influenza, and the cells that repair the damaged lungs are not understood at the single cell level. Such knowledge could help to identify therapeutic targets for intervention, such as novel drugs to prevent viral infection and new treatments to ameliorate morbidity.

Many tumors contain mixed populations of cancer cells that might differ with respect to their signaling pathways that they use for their growth and survival. Since these cancer cells differ with respect to their response to a particular therapy, resistance of a particular population of cancer stem cells contributes to relapse after cytoxic radiotherapy and chemotherapy. As such, treatment failures in the clinic may be due partly to the resistance of a particular population of cancer cells to therapy The often-observed initial shrinkage of a tumor soon after treatment may reflect nothing more than relative sensitivity of one sub population of cancer cells, which could comprise the bulk of a tumor, and may not be important to long term survival. Thus, the most important clinical variable for assessing treatment response and prognosis may not be the absolute tumor size but rather the absolute number of a particular population of cancer cells remaining after treatment. If one could identify differences in the signaling pathways used by these different populations of cancer cells within a tumor, then one could design therapies that target each population of cells. By targeting all populations, one could eliminate a tumor by treating with drugs that affect each different population.

As another example, inflammatory bowel disease results in disruption of the normal structure of the intestine resulting in problems such as diarrhea, bleeding and malabsorption. These problems are caused by destruction of the normal mucosal lining of the gut. The mucosal lining of the colon consists of crypts, where goblet cells, stem cells and progenitor cells are at the base of the crypt, while the mature cells including enterocytes and goblet cells reside at the top of the crypt. With inflammatory bowel disease, it is not clear which cell populations are damaged and the signaling pathways that are required to repair the damaged mucosa.

Methods of precisely determining the number and phenotype of cells in disease lesions using small numbers of cells is of great interest for prognosis, diagnosis identification of signaling pathways that can be targeted by specific therapeutics, of multiple diseases, including inflammatory bowel disease, infections, cancers, autoimmune diseases such as rheumatoid arthritis, and infections. The present invention addresses this issue.

SUMMARY OF THE INVENTION

Compositions and methods are provided for the use of single cell gene expression profiling and/or transcriptome analysis. One method provided herein is a method of identifying different cell populations in a heterogeneous solid tumor sample, comprising: randomly partitioning individual cells from the tumor into discrete locations; performing transcriptome analysis on a plurality of genes of the individually partitioned cells in the discrete locations; and performing clustering analysis to identify one or more different cell populations. In some instances, the individual cells are not enriched prior to partitioning. Transcriptome analysis can be performed on at least 1000 individual cells simultaneously. Transcriptome analysis can be performed using nucleic acid analysis. The discrete locations can be on a planar substrate.

In some embodiments, the random partitioning is performed in a microfluidic system. Transcriptome analysis can comprise analyzing expressed RNA, non-expressed RNA, or both. Transcriptome analysis can be whole transcriptome analysis. Transcriptome analysis can comprise amplifying RNA using a single set of primer pairs, which in some embodiments are not nested primers. Transcriptome analysis can be performed simultaneously or substantially in real time on all or a subset of individual cells. The one or more cell populations can be normal stem cells, normal progenitor cells, normal mature cells, inflammatory cells, cancer cells, cancer stem cells or non-tumorigenic stem cells.

Further provided herein is a method of analyzing a heterogeneous tumor biopsy from a subject, comprising: randomly partitioning cells from the biopsy into discrete locations; performing transcriptome analysis on at least 50 genes of the individually partitioned cells; and using transcriptome data to identify one or more characteristic of the tumor. The performing step can be performed without prior enrichment of a cell type. A characteristic identified can be the presence, absence, or number of cancer cells. A characteristic identified can also be the presence, absence or number of stem cells, early progenitor cells, initial differentiated progenitor cells, late differentiated progenitor cells, or mature cells. A characteristic identified can also be effectiveness of a therapeutic agent in eliminating one or more of the cells. A characteristic identified can also be activity of a signaling pathway, for example, a pathway specific to a cancer stem cell, a differentiated cancer cell, a mature cancer cell, or combination thereof. A method disclosed herein can further comprise the step of using the characteristic to diagnose a subject with cancer or a cancer stage.

Another method disclosed herein is a method of identifying a signaling pathway utilized by a disease-state cell, comprising: randomly partitioning cells from a heterogeneous sample; performing transcriptome analysis on the partitioned cells; using transcriptome analysis to identify at least one disease-state cell; comparing the transcriptome analysis of the at least one disease-state cell to transcriptome of: a) a non-disease state cell; b) a different disease-state cell; and c) a disease-state stem cell; and identifying a signaling pathway that is expressed in (i) the disease-state cell, (ii) the disease-state stem cell, and (iii) optionally in the different disease-state cell, but not in a non-disease-state cell, thereby identifying a signaling pathway utilized by a disease-state cell. The disease state can be cancer, ulcerative colitis or inflammatory bowel disease. In some embodiments, the signaling pathway is required for survival of said disease state cell.

The present disclosure also provides method for diagnosing a subject with a condition comprising: randomly partitioning cells from a heterogeneous sample; performing a first transcriptome analysis on partitioned cells; using transcriptome analysis to identify at least one disease-state cell by comparing the first transcriptome analysis from the at least one disease-state cell to a second transcriptome analysis from a non-disease state cell, thereby diagnosing the presence or absence of a condition associated with the disease state cell in said subject. The disease state can be breast cancer, colon cancer, ulcerative colitis or inflammatory bowel disease. Transcriptome analysis can comprise analyzing expressed RNA, non-expressed RNA, or both. Transcriptome analysis can be whole transcriptome analysis.

Yet another method provided herein is a method for screening for a therapeutic agent comprising: exposing a first subject with disease-state cells to one or more test agents; obtaining a heterogeneous tumor biopsy from the subject from a region of interest; performing transcriptome analysis on at least one individual cell from the heterogeneous tumor biopsy, wherein the biopsy comprises one or more disease state cells; and comparing the transcriptome analysis to a transcriptome derived from either: (i) a second subject without the disease-state cells; or (ii) the first subject prior to said exposing step; and identifying an agent that affect a transcriptome of cells from the test area to be more like those of the second subject or the first subject prior to exposure. The condition can be breast cancer, colon cancer, ulcerative colitis, or inflammatory bowel disease. A therapeutic agent can be an antibody or antibody fragment, small molecule, nucleic acid (for example an siRNA), RNA, DNA, RNA-DNA chimera, protein, or peptide.

The present disclosure also provides a method of determining the potential effectiveness of a therapeutic agent against a disease, comprising: separating a first population of disease-state cells into individual locations, wherein the individual locations comprise an individual cell; determining the expression level of at least one nucleic acid or protein from at least one of the individual cells, thereby producing a disease-state expression signature; exposing a second population of disease state cells to an agent; separating the second population of disease-state cells into individual locations, wherein the individual locations comprise an individual cell; determining the expression level of at least one nucleic acid or protein from at least one of the individual cells from the second population; and comparing the expression level from the individual cell from the second population to the disease-state expression signature, thereby determining the effectiveness of the agent against the disease. The exposing step can be performed in vivo. In some instances, the first population and the second population are isolated from a subject, for example, a human. The disease can be cancer, ulcerative colitis or inflammatory bowel disease. The nucleic acid or the protein can be a cancer cell marker, a cancer stem cell marker or both. An expression level can be an mRNA expression level. In some embodiments, determining the mRNA expression level comprises detection of expression or lack of expression of 10 or more nucleic acids. An expression level can also be a protein expression level. The separating steps can comprise exposing the population of cells to an antibody that specifically binds a protein present on the individual cells.

Further provided herein is a method of determining likelihood of a response by a subject to a therapeutic agent, comprising: separating a population of cells from a subject into individual locations, wherein the individual locations comprise an individual cell and wherein at least one of the individual cells is a disease-state cell; determining the expression level of at least one nucleic acid or protein from at least one of the disease-state individual cells, wherein the nucleic acid or protein is a target of a therapeutic agent; and determining likelihood of a response by a subject based on the expression level of the at least one nucleic acid or protein. An expression level can be an mRNA expression level. In some embodiments, determining the mRNA expression level comprises detection of expression or lack of expression of 10 or more nucleic acids. An expression level can also be a protein expression level. The separating steps can comprise exposing the population of cells to an antibody that specifically binds a protein present on the individual cells. The therapeutic agent can be an anti-cancer agent.

Another method detailed herein provides a prognostic or diagnostic method utilizing gene expression from individual cells, comprising the steps of separating cells from a heterogeneous sample into separately addressable positions; lysing individual cells, and dividing the resulting lysates into at least two portions; amplifying mRNA or cDNA derived therefrom from the individual cells; determining gene expression profiles from one of the lysate portions, wherein the gene expression profile provides sub-population information; and performing transcriptome analysis on at least one cell in a target sub-population. In some methods, at least $10^2$ or at least $10^3$ individual cells are analyzed. Cells can be sorted for expression of at least one cell surface marker. Cells analyzed by the methods disclosed herein can be stem cells, for example hematopoietic stem cells. Initial samples can comprise less than $10^6$ cells or less than $10^5$ cells. Cells can be sorted for expression of at least one of CD34 and Thy1. In some embodiments, expression of at least one or at least five (5) hematopoietic stem cell associated gene is determined. Transcriptome analysis is whole transcriptome analysis.

Further provided herein is a method of classifying a stem cell, comprising the steps of: (a) obtaining a stem cell transcriptome profile from a sample; and (b) comparing the obtained transcriptome profile to a reference stem cell transcriptome profile. A transcriptome profile can comprise a dataset obtained from at least about 5 stem cell-associated proteins. Stem cells analyzed can be cancer stem cells, hematopoietic stem cells, intestinal stem cells, leukemia stem cells, or lung stem cells. Samples analyzed can include cells from a cancer, for example a breast carcinoma, or colon carcinoma. Transcriptome profile analysis can also comprise the additional steps of: extracting mRNA from a sample of stem cells; quantitating the level of one or more mRNA species corresponding to stem cell specific sequences; and comparing the level of one or more mRNA species to the level of said mRNA species in a reference sample.

Also provided herein is a method of collecting data regarding a transcriptome, comprising the steps of: collecting data regarding a transcriptome using any of the methods described herein and sending said data to a computer. A computer can be connected to a sequencing apparatus. Data corresponding to a transcriptome can further be stored after sending, for example the data can be stored on a computer-readable medium which can be extracted from the computer. Data can be transmitted from the computer to a remote location, for example, via the internet.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 1. Single-cell gene expression analysis by real-time PCR of human "colorectal cancer stem cells" ($EpCAM^{high}$) purified from human colorectal cancer tissues xenografted in NOD/SCID mice (tumor #4m6). In the first experiment (panel A), 16 single-cells have been analyzed for the expression of 5 genes, performing 27 replicates for each cell-gene combination; in this experiment, each mRNA preparation from an individual single-cell is used in 3 consecutive rows of the reaction matrix, and each gene-specific primer set is used in 9 consecutive columns, with the only exception of the first three where no primers were added; the levels of gene expression for each individual cell can be visualized as 3×9 blocks using a color scale. In the second experiment (panel B), a similar approach was followed, whereas 16 single-cells have been analyzed for the expression of 16 genes, performing 9 replicates for each cell-gene combination; in this second case, each mRNA preparation from an individual single-cell is used in 3 consecutive rows of the reaction matrix, and each gene-specific primer set is used in 3 consecutive columns, so that the levels of gene expression for each individual cell can be visualized as 3×3 blocks using a color scale. In both cases, the: assay displays a high level of reproducibility and consistency within each set of replicates.

FIG. 4. The CT values of real-time PCR analysis for microRNAs (miRs) levels comparing primary TICs and MTICs.

DETAILED DESCRIPTION

Figure 2A:
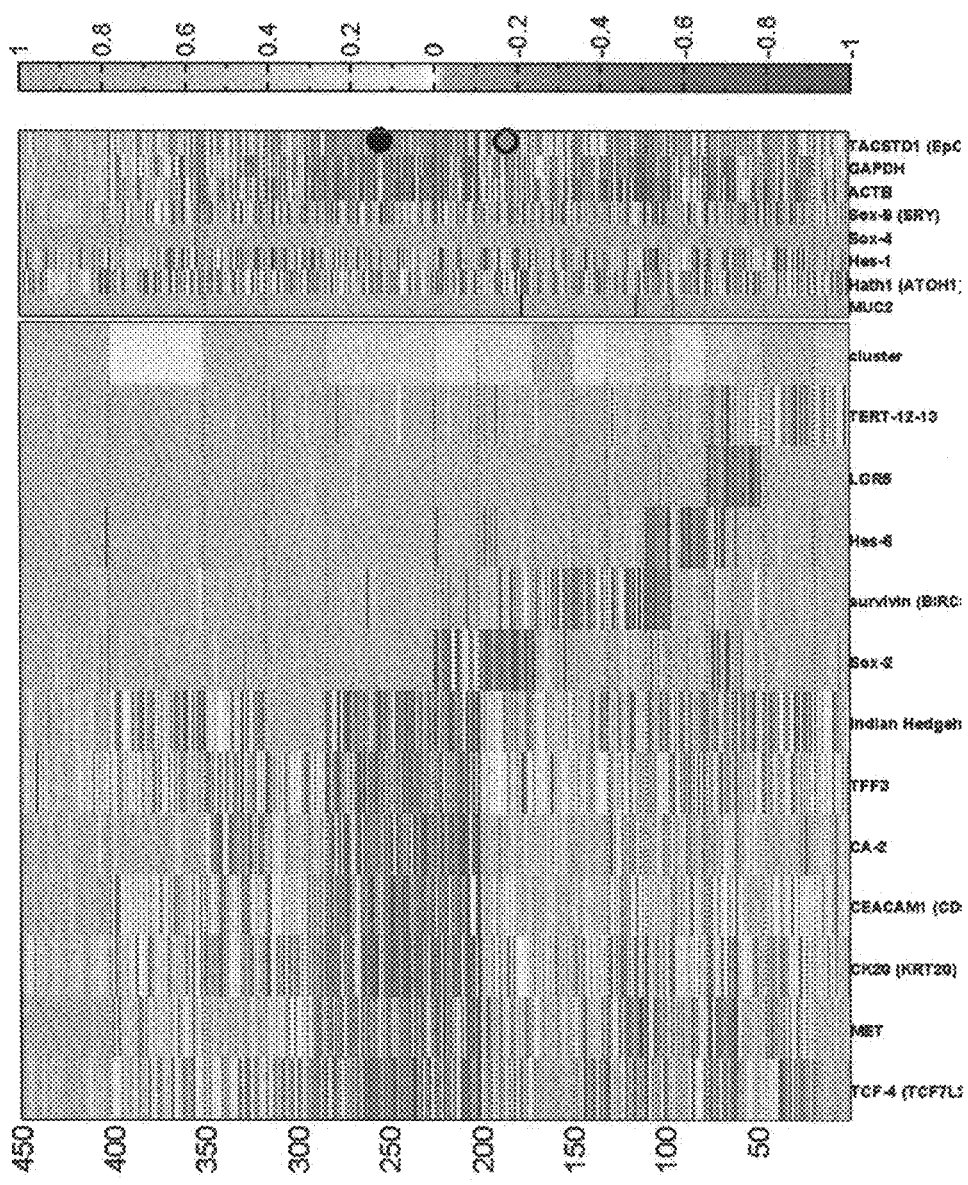
FIG. 2. Single-cell gene-expression analysis by real-time PCR of human "colorectal cancer stem cells" ($EpCAM^{high}/CD166^+$ cells, from xenograft #8m3). In this figure each row identifies a single cell and each column identifies a distinct gene. The intensity of gene expression is depicted using a color code, where darker red indicates stronger intensity and darker green weaker intensity. The analysis clearly shows that, based on their transcriptional repertoire, $EpCAM^{high}/CD166^+$ tumor cells can be subdivided into distinct subsets. Most importantly, cell subsets that show coordinated and simultaneous expression of high levels of genes encoding for terminal differentiation markers of the colonic epithelium (e.g. Cytokeratin 20, CD66a/CEACAM1, Carbonic Anhydrase II, MUC2, Trefoil Family Factor 3) do not express or express lower levels of genes encoding for candidate intestinal stem cell markers or genes known to be necessary for stem cell function (e.g. hTERT, LGR5, Survivin) and vice-versa.

The methods of the invention utilize single cell gene expression profiling of primary cells for characterization of populations of cells for disease diagnosis, sensitivity to a particular therapeutic intervention, prognostic applications, and identification of novel drug targets. A heterogeneous cell sample is divided into spatially separated single cells, which are optionally sorted for properties of interest (possibly including surface markers), then lysed and the contents amplified and individually analyzed for expression of genes of interest. The cells thus analyzed are classified according to the genetic signatures of individual cells. Such classification allows an accurate assessment of the cellular composition of the test sample.

Conventional methods of analyzing single cells for diagnostic purposes include the use of Coulter counters and flow cytometry to count the number of cells of a given type. However, these measurements are typically based on using antibodies to surface markers and do not assay gene expression at the mRNA level or protein expression. Previous examples of single cell PCR analysis exist, but these were performed on too small a number of cells and or genes to provide useful diagnostic information or to provide the ability to discriminate fine or related subpopulations of cells within a tissue. Tissue-staining methods used by pathologists suffer from similar drawbacks and depend strongly on qualitative judgments by the pathologist. Moreover, these measurements are limited to measuring a small number of parameters. The methods of the present invention, however, allow the measure of at least 10, at least 15, at least 20, at least 50, at least 100, at least 200, at least 300, at least 400, at least 500, or more different parameters, where parameters include mRNA expression, gene expression, protein expression and may further include cell surface markers in combination with mRNA, gene and/or protein expression.

Before the subject invention is described further, it is to be understood that the invention is not limited to the particular embodiments of the invention described below, as variations of the particular embodiments may be made and still fall within the scope of the appended claims. It is also to be understood that the terminology employed is for the purpose of describing particular embodiments, and is not intended to be limiting. In this specification and the appended claims, the singular forms "a," "an" and "the" include plural reference unless the context clearly dictates otherwise.

Where a range of values is provided, it is understood that each intervening value, to the tenth of the unit of the lower limit unless the context clearly dictates otherwise, between the upper and lower limit of that range, and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood to one of ordinary skill in the art to which this invention belongs. Although any methods, devices and materials similar or equivalent to those described herein can be used in the practice or testing of the invention, illustrative methods, devices and materials are now described.

All publications mentioned herein are incorporated herein by reference for the purpose of describing and disclosing the subject components of the invention that are described in the publications, which components might be used in connection with the presently described invention.

Identification and Classification of Cells into Populations and Subpopulations

The present disclosure is directed to methods of classification of identifying populations and subpopulations of cells and using populations and/or subpopulations to diagnose, prognose and/or identify therapeutic targets for conditions such as diseases. Diseases can include cancers of any sort (including but not limited to, solid tumors, breast cancer, colon cancer, lung cancer, leukemia), inflammatory bowel disease, ulcerative colitis, autoimmune diseases, inflammatory diseases and infectious diseases. The present disclosure also provides reagents and kits for use in practicing the subject methods, such as antibody and nucleic acid probes useful in detecting any of the biomarkers described herein, or reagents that modulate the biomarkers herein. The methods may also determine an appropriate level of treatment for a particular cancer.

Isolation of Single Cells

Single cell gene expression profiling is provided for disease diagnostic or prognostic applications, as well as a research tool to identify novel drug targets. Diseases of interest include, without limitation, immune-mediated dysfunction, cancer, and the like. In the methods of the invention, a heterogeneous cell mixture, e.g. a tumor needle biopsy, inflammatory lesion biopsy, synovial fluid, spinal tap, etc., is divided randomly or in a certain order into spatially separated single cells, e.g. into a multiwell plate, microarray, microfluidic device, or slide. Cells are then lysed, and the contents amplified and individually analyzed for expression of genes of interest. The cells thus analyzed are classified according to the genetic signatures of individual cells. Such classification allows an accurate assessment of the cellular composition of the test sample, which assessment may find use, for example, in determining the identity and number of cancer stem cells in a tumor; in determining the identity and number of immune-associated cells such as the number and specificity of T cells, dendritic cells, B cells and the like.

In some embodiments, the cell sample to be analyzed is a primary sample, which may be freshly isolated, frozen, etc. However, cells to be analyzed can be cultured cells. Usually the sample is a heterogeneous mixture of cells, comprising a plurality of distinct cell types, distinct populations, or distinct subpopulations, for example 2, 3, 4, 5, 6, 7, 8, 9, 10, 11, 12, 13, 14, 15, 16, 17, 18, 19, 20 or more cell types, populations, or subpopulations. In some embodiments the sample is a cancer sample from a solid tumor, leukemia, lymphoma, etc., which may be a biopsy, e.g. a needle biopsy, etc., a blood sample for disseminated tumors and leukemias, and the like. Samples may be obtained prior to diagnosis, may be obtained through a course of treatment, and the like.

For isolation of cells from tissue, an appropriate solution can be used for dispersion or suspension. Such solution will generally be a balanced salt solution, e.g. normal saline, PBS, Hank's balanced salt solution, etc., conveniently supplemented with fetal calf serum or other naturally occurring factors, in conjunction with an acceptable buffer at low concentration, generally from 5-25 mM. Convenient buffers include. HEPES, phosphate buffers, lactate buffers, etc. The separated cells can be collected in any appropriate medium that maintains the viability of the cells, usually having a cushion of serum at the bottom of the collection tube. Various media are commercially available and may be used according to the nature of the cells, including dMEM, HBSS, dPBS, RPMI, Iscove's medium, etc., frequently supplemented with fetal calf serum.

In some embodiments, cells in a sample are separated on a microarray. For example, a highly integrated live-cell microwell microarray system may utilize microwells each of which is just large enough to fit a single cell (see Tokimitsu et al. (2007) Cytometry Part A 71k 1003:1010; and Yamamura et al. (2005) Analytical Chemistry 77:8050; each herein specifically incorporated by reference). Prior enrichment of cells of interest—such as by FACS or other sorting—is optional and in some embodiments, cells from a sample are divided into discrete locations without any prior sorting or enrichment. For example, cells from a sample (e.g., blood sample, biopsy, solid tumor) can be individually isolated into distinct positions. Typically, for solid tissue samples, the samples are mechanically, chemically, and/or enzymatically separated (e.g., by treatment with trypsin or sonication). Cells from a sample can be placed into any cell sorting device (e.g., a microfluidic cell sorter) such that individual cells are isolated, such as at an addressable position on a planar surface. Planar surfaces can have indentations, barriers or other features ensuring isolation of individual cells. Isolated cells can then be analyzed according to the methods herein. Preferably, cells are separated into distinct positions wherein each position contains 1 or 0 cells.

Cells are optionally sorted, e.g. by flow cytometry, prior to the separation. For example, FACS sorting or size-differential sorting, can be used to increase the initial concentration of the cells of interest by at least 1,000, 10,000, 100,000, or more fold, according to one or more markers present on the cell surface. Such cells are optionally sorted according to the presence and/or absence of cell surface markers particularly markers of a population or subpopulation of interest.

Where the cells are isolated into distinct positions for analysis, the cells may be sorted with a microfluidic sorter, by flow cytometry, microscopy, etc. A microfabricated fluorescence-activated cell sorter is described by Fu et al. (1999) Nature Biotechnology 17: 1109 and Fu et al. (2002) Anal. Chem. 74:2451-2457, each herein specifically incorporated by reference. A sample can be sorted with an integrated microfabricated cell sorter using multilayer soft lithography. This integrated cell sorter may incorporate various microfluidic functionalities, including peristaltic pumps, dampers, switch valves, and input and output wells, to perform cell sorting in a coordinated and automated fashion. The active volume of an actuated valve on this integrated cell sorter can be as small as 1 pL, and the volume of optical interrogation as small as 100 fL. Compared with conventional FACS machines, the microfluidic FACS provides higher sensitivity, no cross-contamination, and lower cost.

Individual cells can be isolated into distinct positions (e.g., a 96-well plate or a microarray address) for further analysis and/or manipulation. For example, a cell population containing hematopoietic stem cells (HSCs) is sorted by FACS analysis utilizing antibodies capable of distinguishing HSCs from mature cells. The cells are sorted into 96-well plates, lysed by appropriate methods and the lysates are analyzed by qPCR, microarray analysis, and/or sequencing.

Devices for single cell isolation include a microfluidic cell sorter, which isolates live cells from cellular debris and sorts cells from a single cell suspension. Microfluidic devices can be used in combination with fluorescent signals (e.g., labeled antibodies to markers for a target population or subpopulation) from 1, 2, 3, 4, 5 or more different surface markers, and places them in individual bins for subsequent genetic studies. Other upstream steps such as digesting the tumor or cell culture to obtain a cell suspension and staining the cells with fluorescent surface markers may be incorporated in this system. The number of cells to be analyzed depends on the heterogeneity of the sample, and the expected frequency of cells of interest in the sample. Usually at least about $10^2$ cells are analyzed, at least about $10^3$, at least $5\times10^3$, at least about $10^4$, at least about $10^5$, at least a about $10^6$, at least about $10^7$, at least about $10^8$, at least about $10^9$, at least about $10^{10}$, at least about $10^{11}$, at least about $10^{12}$, at least about $10^{13}$, at least about $10^{14}$, at least about $10^{15}$, or more cells are analyzed.

In some instances, a single cell analysis device (SCAD) is modular and can perform the following steps in an integrated, fully automated fashion 1) Digestion of the tissue. The tissue is placed in the input port of the device. Appropriate enzymes are introduced in the device and flowed to perform the digestion of the extracellular matrix in order to obtain a cell suspension. 2) Separation of live cells from the debris, for example by flowing a digested sample suspension through a microfluidic "metamaterial," which allows splitting the fluidic flow according to the size of the particles. 3) Staining. The filtered single cell suspension is optionally stained using appropriate surface markers in a compartment of the microfluidic device. Staining with up to five different markers may be useful in obtaining a high purity population of cancer cells. 4) Sorting. The stained single-cell suspension is flowed into the next compartment of the microfluidic device to sort out the cancer cells from the rest of the cells. Various embodiments of sorters are described in the Examples.

Expression Profiling

Sorted cells can be individually lysed to perform analysis of genetic (RNA, DNA) and/or protein composition of the cells. mRNA can be captured on a column of oligo-dT beads, reverse transcribed on beads, processed off chip, transferred to a macroscopic well, etc. Optionally, DNA or RNA is preamplified prior to analysis. Preamplification can be of an entire genome or transcriptome, or a portion thereof (e.g., genes/transcripts of interest). A polynucleotide sample can be transferred to a chip for analysis (e.g., by qRT-PCR) and determination of an expression profile.

The term "expression profile" is used broadly to include proteins expressed and/or nucleic acids expressed. A nucleic acid sample includes a plurality or population of distinct nucleic acids that can include the expression information of the phenotype determinative genes of interest of the individual cell. A nucleic acid sample can include RNA or DNA nucleic acids, e.g., mRNA, cRNA, cDNA, etc. Expression profiles can be generated by any convenient means for determining differential gene expression between two samples, e.g. quantitative hybridization of mRNA, labeled mRNA, amplified mRNA, cRNA, etc., quantitative PCR, and the like. A subject or patient sample, e.g., cells or collections thereof, e.g., tissues, is assayed. Samples are collected by any convenient method, as known in the art. Additionally, tumor samples can be collected and tested to determine the relative effectiveness of a therapy in causing differential death between normal and diseased cells. Genes/proteins of interest are genes/proteins that are found to be predictive, including the genes/proteins provided herein, where the expression profile may include expression data for 5, 10, 20, 25, 50, 100 or more (including all) of the listed genes/proteins.

The sample can be prepared in a number of different ways, as is known in the art, e.g., by mRNA isolation from a single cell, where the isolated mRNA is used as is, amplified, employed to prepare cDNA, cRNA, etc., as is known in the differential expression art (for example, see Marcus, et al., Anal. Chem. (2006); 78(9): 3084-89). The sample can be prepared from any tissue (e.g., a lesion, or tumor tissue) harvested from a subject. Analysis of the samples can be used for any purpose (e.g., diagnosis, prognosis, classification, tracking and/or developing therapy). Cells may be cultured prior to analysis.

The expression profile may be generated from the initial nucleic acid sample using any conventional protocol. While a variety of different manners of generating expression profiles are known, such as those employed in the field of differential gene expression analysis, one representative and convenient type of protocol for generating expression profiles is quantitative PCR (QPCR, or QT-PCR). Any available methodology for performing QPCR can be utilized, for example, as described in Valera, et al., *J. Neurooncol.* (2007) 85(1):1-10.

After obtaining an expression profile from the sample being assayed, the expression profile can be compared with a reference or control profile to make a diagnosis, prognosis, analysis of drug effectiveness, or other desired analysis. A reference or control profile is provided, or may be obtained by empirical methods. An obtained expression profile can be compared to a single reference/control profile to obtain information regarding the phenotype of the cell/tissue being assayed. Alternately, the obtained expression profile can be compared to two or more different reference/control profiles to obtain more in-depth information regarding the phenotype of the assayed cell/tissue. For example, the obtained expression profile may be compared to a positive and negative reference profile to obtain confirmed information regarding whether the cell/tissue has the phenotype of interest.

Determination or analysis of the difference values, i.e., the difference in expression between two profiles can be performed using any conventional methodology, where a variety of methodologies are known to those of skill in the array art, e.g., by comparing digital images of the expression profiles, by comparing databases of expression data, etc. Patents describing ways of comparing expression profiles include, but are not limited to, U.S. Pat. Nos. 6,308,170 and 6,228,575, the disclosures of which are herein incorporated by reference. Methods of comparing expression profiles are also described herein.

A statistical analysis step can then be performed to obtain the weighted contribution of the set of genes. For example, nearest shrunken centroids analysis may be applied as described in Tibshirani et al. (2002) P.N.A.S. 99:6567-6572 to compute the centroid for each class, then compute the average squared distance between a given expression profile and each centroid, normalized by the within-class standard deviation.

The classification can be probabilistically defined, where the cut-off may be empirically derived. In one embodiment of the invention, a probability of about 0.4 can be used to distinguish between quiescent and induced patients, more usually a probability of about 0.5, and can utilize a probability of about 0.6 or higher. A "high" probability can be at least about 0.75, at least about 0.7, at least about 0.6, or at least about 0.5. A "low" probability may be not more than about 0.25, not more than 0.3, or not more than 0.4. In many embodiments, the above-obtained information about the cell/tissue being assayed is employed to predict whether a host, subject or patient should be treated with a therapy of interest and to optimize the dose therein.

Characterization of Cell Populations and Subpopulations

In some embodiments of the invention, for example with epithelial cancers, including, without limitation, breast cancer and colon cancer, characterization of cancer stem cells according to expression of a cancer stem cell marker (e.g., CD66a) allows for the identification of CSC. There is a subpopulation of tumorigenic cancer cells with both self-renewal and differentiation capacity. These tumorigenic cells are responsible for tumor maintenance, and also give rise to large numbers of abnormally differentiating progeny that are not tumorigenic, thus meeting the criteria of cancer stem cells. Tumorigenic potential is contained within a subpopulation of cancer cells differentially expressing the markers of the present invention. As shown herein, within the population of cells that positively express markers for cancer stem cells, there is heterogeneity, e.g., where cells that are negative for CD66 (CD66$^-$) cells, are enriched for cancer stem cells (tumorigenic), while the CD66a$^+$ cells are not tumorigenic. Detection of such heterogeneity within populations allows for determination of subpopulations.

One of skill in the art will recognize that multiple sequences—representing genes, transcripts and/or proteins—can be analyzed. Such sequences can allow the determination and/or differentiation of the phenotypes of cells within a sample.

Markers, or marker panels, can be chosen on the basis of multiple aspects of a target population or subpopulation within a sample, for example, tissue source (e.g., neuronal vs. epithelial) or disease state (e.g., cancerous vs. non-cancerous). Other sequences useful for distinguishing cell populations (e.g., cancer stem cell from normal cell) can be determined using the methods described herein, such as by detecting changes (e.g., up- or down-regulation) in genes in target populations.

Nucleic acids which are useful in distinguishing one population from another population can be up-regulated or down-regulated as compared between populations. For example, expression of some nucleic acids are up-regulated or down regulated in cancer versus normal cells, stem cells versus differentiated cells, and cancer stem cells versus differentiated cancer cells. In some instances up- or down-regulation of genes can be used to distinguish sub-populations within larger populations. For example, some nucleic acids are expressed in normal cells only, normal cells and cancer stem cells, or cancer stem cells only.

Nucleic acids can be up-regulated or down-regulated as compared to another population or subpopulation, a particular nucleic acid of known expression level, or a standard expression level. Alternately, when analyzing the expression of multiple genes, a heatmap can be created by subtracting the mean and dividing by the standard deviation for each gene independently and numerical values are assigned based on the degree of deviation from the mean. For example, values of +/−1 can represent 2.5-3 standard deviations from the mean. Such analyses can be further refined, such that genes in the "+/−3" range can be used to cluster different types of populations (e.g., cancer is given the value "+3" and normal tissue is given the value "−3" so that a clustering algorithm can discern between them). An upregulated gene may be a "+" value.

In some instances, combinations of differentially expressed nucleic acids can be used as profiles for a particular population or subpopulation. Profiles can comprise any number of differentially expressed nucleic acids and/or proteins, for instance, at least 1, 2, 3, 4, 5, 6, 7, 8, 9, 10, 11, 12, 13, 14, 15, 16, 17, 18, 19, 20, 25, 30, 35, 40, 45, 50 or more nucleic acids and/or proteins. In some instances, a nucleic acid utilized to identify a target population or subpopulation can be similarly expressed in a target and a non-target population or non-target subpopulation. Such similarly expressed nucleic acids will generally be utilized in combination with other differentially expressed nucleic acids to identify a target population or subpopulation.

The methods described herein can be used to analyze a heterogenous cell population from any source (e.g., biopsy, normal tissue, solid tumor, etc.). Such methods can be used to isolate and analyze any cell population, for example a target population within the larger heterogenous population or subpopulation, a heterogenous population or subpopulation for the presence of a target cell, cancer or other stem cells, or an entire heterogenous population.

Biomarker Discovery

The methods disclosed herein allow for determining new markers which are associated with a cell population or sub-population (e.g., normal cells, cancer cells, disease-state cells). Markers can include any biomarker including, but not limited to DNA, RNA and proteins. In some instances, a marker for a cell population is a gene or mRNA not normally expressed in a given cell (e.g., expression of a stem cell gene by a progenitor cell or a cell expressing differentiation markers or expression of proliferation genes by cells also expressing differentiation markers). Typically, more than one marker is assessed, for example, 2, 3, 4, 5, 6, 7, 8, 9, 10, 11, 12, 13, 14, 15; 16, 17, 18, 19, 20, 30, 40, 50, 60, 70, 80, 90, 100, 200, 300, 400, 500, 600, 700, 800, 900, 1000 or more markers. Where markers are expressed RNAs, any portion of a transcriptome can be determined, up to and including the whole transcriptome.

Analysis of expression patterns of nucleic acids in certain target cell populations or subpopulations can lead to identification of new biomarkers which distinguish the target population or subpopulation from others. For example, where a unique surface-marker protein is expressed in a target population or subpopulation, an antibody which binds to that marker can be developed for use in isolating and/or identifying cells of that population or subpopulation in the same or other individuals (e.g., by FACS). Identification of population or subpopulation specific biomarkers includes the absence of certain markers on cell populations or subpopulations which would allow for negative selection. The presence of markers in a population or subpopulation can be determined using the methods described herein and can be used to define a cell population. mRNAs in analyzed cell populations or subpopulations have shown that certain genes are differentially expressed in normal and cancer cells. Differential expression can include increases or decreases in transcript level, lack of transcription, and/or altered regulation of expression (e.g., a different pattern of expression in response to a stimulus). mRNAs or other markers which serve as markers for a cell population or subpopulation can also comprise mutations which are present in that cell population or subpopulation (e.g., cancer cells and cancer stem cells, but not normal cells). One of skill in the art will recognize that such markers can represent a cell population from a single individual tested and/or may represent markers for many individuals. In some instances, the expressed mRNAs are translated into proteins which can be detected by any of a wide array of protein detection methods (e.g., immunoassay, Western blot, etc.).

Other markers which can be detected include microRNAs. In some instances, expression levels of microRNAs serve as a marker for a cell population where the expression of a particular microRNA is at increased or decreased by about 1.5, 1.6, 1.7, 1.8, 1.9, 2.0, 2.1, 2.2, 2.3, 2.4, 2.5, 2.6, 2.7, 2.8, 2.9, 3.0 or more fold as compared to a similar cell population.

Determination of Transcriptomes in Cell Populations and Subpopulations

To gain further information regarding the cells isolated by any of the methods of the present invention (e.g., FACS separation of cells from a population, followed by partial transcriptional analysis), it can be advantageous to further analyze cells. In some instances, individual cells isolated from a sample (e.g., by isolation of individual cells, with or without prior enrichment), are lysed and nucleic acids of interest (e.g., genomic DNA, mRNA, etc.) are collected. As described herein, transcriptional analysis of a gene or panel of genes can be utilized to categorize the isolated cells into groups which show similarities in their expression profiles (e.g., cancer stem cells vs. non-stem cells). Without being bound by theory, such information can suggest functional differences as the genes a cell is transcribing are tightly associated with its function. Once cells are organized into like-cell groups (e.g., those cells demonstrating similar or identical transcriptional profiles), lysates from individual cells and/or lysates comprising pooled nucleic acids from like-cells can be further analyzed at the transcriptome level. In some instances lysates (e.g., single-cell or like-cell pools) are subjected to methodologies (e.g., high-throughput sequencing) to define a portion of the transcriptome of each cell and/or like-cell pools. Transcriptome information from individual cells can be analyzed at the population level by comparing and/or combining the results from individual cells with the results from other like cells. Transcriptome information from like-cell pools can also be used to define the transcriptional characteristics of such pools.

Any cell population can be studied in such a manner, for example cell populations comprising stem cells. In some embodiments, cells include stem cells, including embryonic stem cells, adult stem cells—including, but not limited to cancer stem cells, hematopoietic stem cells (HSCs) and mesenchymal stem cells—and induced pluripotent stem cells. Generally, a cell population is a heterologous population (e.g., a clinical specimen). Sub-populations of interest within a larger cell population can be isolated by any method herein (e.g., FACS sorting) according to any relevant criteria (e.g., surface protein expression). In some embodiments, such sorted cells are compartmentalized such that each sorted population comprises 10 or fewer cells, 5 or fewer cells, 4 cells, 3 cells, 2 cells or 1 cell.

In some embodiments, cells are lysed and a split into two or more portions. One portion of the lysate is further analyzed (e.g., analysis of a panel of genes to detect expression) to detect and/or differentiate sub-populations within the larger heterologous population. Lysates from cells indicated to be in the sub-population of interest (e.g., hematopoietic stem cells) are further analyzed. Lysates from individual cells, or pooled lysates from like-cells can be analyzed. Determination of "like-cell" populations can be based on similarities in the expression of 1, 2, 3, 4, 5, 6, 7, 8, 9, 10, 15, 20, 25, 30, 35, 40, 45, 50, 55, 60, 65, 70, 75, 80, 85, 90, 100, 200, 300, 400, 500, 600, 700, 800, 900, 1000 or more genes.

Cells and cell populations or subpopulations of interest can be further analyzed. Cell populations or subpopulations can comprise cells which comprised a portion of the original sample, for example cells which comprised 1%, 2%, 3%, 4%, 5%, 6%, 7%, 8%, 9%, 10% or more of the original sample. Using the methods described herein, cell populations or subpopulations of interest can be isolated from heterogenous samples such that the isolated populations or subpopulations can be 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100% free of cells which are not members of the target population or subpopulation. As lysates are prepared from cells which are isolated from the original population, study of like-cell populations can be accomplished by pooling lysates from like-cells.

Further analysis of cells, populations and/or subpopulations can include whole transcriptome analysis. In some instances, lysates will comprise mRNA which can be amplified (e.g., cDNA) for analysis, or directly analyzed (e.g, mRNA sequencing, microarray analysis). mRNA amplification can be performed by any method known in the art (e.g, in vitro transcription, ligation-PCR cDNA amplification). In some embodiments, mRNA amplification can be performed in, or with the use of, a microfluidic device. Whole transcriptome analysts can be performed by sequencing platforms, such as those commercially available from Illumina (RNA-Seq) and Helicos (Digital Gene Expression or "DGE"). In some embodiments, polynucleotides of interest are sequenced. Target nucleic acids may be sequenced by conventional gel electrophoresis-based methods using, for example, Sanger-type sequencing. Alternatively, sequencing may be accomplished by use of several "next generation" methods. Such "next generation" sequencing methods include, but are not limited to those commercialized by: 1) 454/Roche Lifesciences including but not limited to the methods and apparatus described in Margulies et al., Nature (2005) 437:376-380 (2005); and U.S. Pat. Nos. 7,244,559; 7,335,762; 7,211,390; 7,244,567; 7,264,929; 7,323,305; 2) Helicos BioSciences Corporation (Cambridge, Mass.) as described in U.S. application Ser. No. 11/167,046, and U.S. Pat. Nos. 7,501,245; 7,491,498; 7,276,720; and in U.S. Patent Application Publication Nos. US20090061439; US20080087826; US20060286566; US20060024711; US20060024678; US20080213770; and US20080103058; 3) Applied Biosystems (e.g. SOLiD sequencing); 4) Dover Systems (e.g., Polonator G.007 sequencing); 5) Illumina as described U.S. Pat. Nos. 5,750,341; 6,306,597; and 5,969, 119; and 6) Pacific Biosciences as described in U.S. Pat. Nos. 7,462,452; 7,476,504; 7,405,281; 7,170,050; 7,462,468; 7,476,503; 7,315,019; 7,302,146; 7,313,308; and US Application Publication Nos. US20090029385; US20090068655; US20090024331; and US20080206764. All references are herein incorporated by reference. Such methods and apparatuses are provided here by way of example and are not intended to be limiting.

Whole transcriptome analysis can be performed for multiple reasons which allow further characterization of different cellular sub-populations, including but not limited to: 1) detecting activity of genes that can reveal unique biological properties of subpopulations and/or transcription factors controlling their development; 2) locating and/or characterizing surface markers which may be used to purify the sub-populations (e.g. by FACS sorting); and 3) detecting and/or characterizing cellular genes and/or gene products as potential drug targets for disease which distinguish the sub-population from the general population (e.g., cancer stem cells vs. normal tissue).

Analysis of populations and/or subpopulations (e.g., by transcriptome analysis) can allow for the refining of techniques for isolating cells which belong to the sub-population. For example, where the methods reveal a sub-population specific surface antigen, antibodies developed by any available antibody synthesis method can be used to isolate such cells from a heterologous population (e.g., patient sample). Additionally, transcriptome profiles can be used to develop gene expression panels which can be used to identify cells from other populations (e.g., samples from the same or different patients).

Diagnostics and Prognostics

The invention finds use in the prevention, treatment, detection or research into any condition, including cancer, inflammatory diseases, autoimmune diseases and infections. Examples of cancer include prostrate, pancreas, colon, brain, lung, breast, bone, and skin cancers. Examples of inflammatory conditions include irritable bowel syndrome and ulcerative colitis. Examples of autoimmune diseases include Chrohn's disease, lupus, and Graves' disease. For example, the invention finds use in the prevention, treatment, detection of or research into gastrointestinal cancers, such as cancer of the anus, colon, esophagus, gallbladder, stomach, liver, and rectum; genitourinary cancers such as cancer of the penis, prostate and testes; gynecological cancers, such as cancer of the ovaries, cervix, endometrium, uterus, fallopian tubes, vagina, and vulva; head and neck cancers, such as hypopharyngeal, laryngeal, oropharyngeal cancers, lip, mouth and oral cancers, cancer of the salivary gland, cancer of the digestive tract and sinus cancer; metastatic cancer; sarcomas; skin cancer; urinary tract cancers including bladder, kidney and urethral cancers; endocrine system cancers, such as cancers of the thyroid, pituitary, and adrenal glands and the pancreatic islets; and pediatric cancers.

Methods are also provided for optimizing therapy, by first classification of individual cells in a sample, and based on that classification information, selecting the appropriate therapy, dose, treatment modality, etc. which optimizes the differential between delivery of an anti-proliferative treatment to the undesirable target cells, while minimizing undesirable toxicity. The treatment is optimized by selection for a treatment that minimizes undesirable toxicity, while providing for effective anti-proliferative activity. Treatment can be selected to affect only a subset of the cells in a sample. In some instances a therapy is selected that affects less than about 5%, less than about 1%, less than about 0.5%, less than about 0.2%, less than about 0.1%, less than about 0.05%, less than about 0.02%, less than about 0.01%, or fewer of the cells in the sample.

A signature for a condition can refer to an expression pattern of one or more genes or proteins in a single cell that indicates the presence of a condition. A cancer stem cell signature can refer to an expression pattern of one or more genes and/or proteins whose expression is indicative of a cancer stem cell phenotype. An autoimmune or inflammatory cell signature refers to genes and/or proteins whose expression is indicative of an autoimmune or inflammatory cell signature. A signature can be obtained from all or a part of a dataset, usually a signature will comprise gene and/or protein expression information from at least about 5 genes and/or proteins, at least about 10 genes and/or proteins, at least about 15 genes and/or proteins, at least about 20 genes and/or proteins, at least about 25 genes and/or proteins, at least about 50 genes and/or proteins, at least about 75 genes and/or proteins, at least about 100 genes and/or proteins, at least about 150 genes and/or proteins, at least about 200 genes and/or proteins, at least about 300 genes and/or proteins, at least about 400 genes and/or proteins, at least about 500 genes and/or proteins, or more genes and/or proteins. Where a subset of the dataset is used, the subset may comprise up-regulated genes, down-regulated genes, or a combination thereof.

Analysis of Patient Samples for Clinical Applications

Although the description below focuses on cancer stem cells, the methods described herein can be used to isolate and/or analyze any cell population, including but not limited to normal cells of any tissue (e.g., normal stem cells, normal progenitor cells, and normal mature cells), virally infected cells, inflammatory cells, progenitor cells, cancer cells (e.g., tumorigenic cells, non-tumorigenic cells, cancer stem cells, and differentiated cancer cells), disease-state cells (e.g., cancer cells, inflammatory bowel disease cells, ulcerative colitis cells, etc.), microbial (bacterial, fungal, protist) cells, etc. Thus, the details provided using cancer stem cells (CSC) are illustrative of analysis that can be performed for any disease state or condition.

In some embodiments of the invention, the number of CSC in a patient sample can be determined relative to the total number of cancer cells. For example, cells from a biopsy sample are isolated and analyzed for expression of one or more mRNAs and/or proteins indicative of a cancer cell and cells that exhibit the CSC phenotype are quantitated. Alternately, data collected for particular populations or subpopulations of CSCs can be used to develop affinity (e.g., antibody) screens for the population or subpopulation and such affinity screens can be used to quantitate the number of cells. Typically, a greater percentage of CSC is indicative of the potential for continued self-renewal of cells with the cancer phenotype. The quantitation of CSC in a patient sample can be compared to a positive and/or negative reference sample, e.g. a patient sample such as a blood sample, a remission patient sample, etc. In some embodiments, the quantitation of CSC is performed during the course of treatment, where the number of cancer cells and the percentage of such cells that are CSC are quantitated before, during and as follow-up to a course of therapy. Desirably, therapy targeted to cancer stem cells results in a decrease in the total number, and/or percentage of CSC in a patient sample.

The CSC can be identified by their phenotype with respect to particular markers, and/or by their functional phenotype. In some embodiments, the CSC are identified and/or isolated by binding to the cell with reagents specific for the markers of interest. The cells to be analyzed may be viable cells, or may be fixed or embedded cells.

The presence of a CSC in a patient sample can also be indicative of the stage of the cancer (e.g., leukemia, breast cancer, prostate cancer). In addition, detection of CSC can be used to monitor response to therapy and to aid in prognosis. The presence of CSC can be determined by quantitating the cells having the phenotype of the stem cell. In addition to cell surface phenotyping, it may be useful to quantitate the cells in a sample that have a "stem cell" character, which may be determined by functional criteria, such as the ability to self-renew, to give rise to tumors in vivo, e.g. in a xenograft model, and the like.

Clinical samples for use in the methods of the invention may be obtained from a variety of sources, particularly blood, although in some instances samples such as bone marrow, lymph, cerebrospinal fluid, synovial fluid, and the like may be used. Samples can include biopsies, or other clinical specimens containing cells. Some samples comprise solid tumors or portions thereof. In instances where cell masses are to be assayed, such masses can be dissociated by any appropriate means known in the art (e.g., enzymatic digestion, physical separation). Such samples can be separated by centrifugation, elutriation, density gradient separation, apheresis, affinity selection, panning, FACS, centrifugation with Hypaque, etc. prior to analysis, and usually a mononuclear fraction (PBMC) is used. In this manner, individual cells from a sample (e.g., solid tumor) can be analyzed for differential gene expression and/or transcriptome analysis as described herein.

Once a sample is obtained, it can be used directly, frozen, or maintained in appropriate culture medium for short periods of time. Various media can be employed to maintain cells. The samples may be obtained by any convenient procedure, such as biopsy, the drawing of blood, venipuncture, or the like. In some embodiments, a sample will comprise at least about $10^2$ cells, more usually at least about $10^3$, $10^4$, $10^5$ or more cells. Typically, the samples are from human patients, although animal models may find use, e.g. equine, bovine, porcine, canine, feline, rodent, e.g. mice, rats, hamster, primate, etc.

An appropriate solution may be used for dispersion or suspension of a cell sample. Such solution will generally be a balanced salt solution, e.g. normal saline, PBS, Hank's balanced salt solution, etc., conveniently supplemented with fetal calf serum or other naturally occurring factors, in conjunction with an acceptable buffer at low concentration, generally from 5-25 mM. Convenient buffers include HEPES, phosphate buffers, lactate buffers, etc.

Analysis of cell staining can be performed using conventional methods. Techniques providing accurate enumeration include fluorescence activated cell sorters, which can have varying degrees of sophistication, such as multiple color channels, low angle and obtuse light scattering detecting channels, impedance channels, etc. The cells may be selected against dead cells by employing dyes associated with dead cells (e.g. propidium iodide).

The affinity reagents may be specific receptors or ligands for the cell surface molecules indicated above. In addition to antibody reagents, peptide-MHC antigen and T cell receptor pairs may be used; peptide ligands and receptors; effector and receptor molecules, and the like. Antibodies and T cell receptors may be monoclonal or polyclonal, and may be produced by transgenic animals, immunized animals, immortalized human or animal B-cells, cells transfected with DNA vectors encoding the antibody or T cell receptor, etc. The details of the preparation of antibodies and their suitability for use as specific binding members are well-known to those skilled in the art.

One approach is the use of antibodies as affinity reagents. Conveniently, these antibodies can be conjugated with a label for use in separation. Labels include any labels known in the art including, but not limited to, magnetic beads, which allow for direct separation, biotin, which can be removed with avidin or streptavidin bound to a support, fluorochromes, which can be used with a fluorescence activated cell sorter, or the like, to allow for ease of separation of the particular cell type. Fluorochromes that find use include phycobiliproteins, e.g. phycoerythrin and allophycocyanins, fluorescein and Texas red. Frequently each antibody is labeled with a different fluorochrome, to permit independent sorting for each marker.

Antibodies can be added to a suspension of cells, and incubated for a period of time sufficient to bind the available cell surface antigens. The incubation will usually be at least about 5 minutes and usually less than about 30 minutes. It is desirable to have a sufficient concentration of antibodies in the reaction mixture, such that the efficiency of the separation is not limited by lack of antibody. The appropriate concentration is determined by titration. The medium in which the cells are separated is any medium that maintains the viability of the cells. One medium which can be utilized is phosphate buffered saline containing from 0.1 to 0.5% BSA. Various media are commercially available and may be used according to the nature of the cells, including Dulbecco's Modified Eagle Medium (dMEM), Hank's Basic Salt Solution (HESS), Dulbecco's phosphate buffered saline (dPBS), RPMI, Iscove's medium, PBS with 5 mM EDTA, etc., frequently supplemented with fetal calf serum, BSA, HSA, etc. The labeled cells can then be quantitated as to the expression of cell surface markers as previously described.

The comparison of a differential progenitor analysis obtained from a patient sample, and a reference differential progenitor analysis can be accomplished by the use of suitable deduction protocols, AI systems, statistical comparisons, etc. A comparison with a reference differential progenitor analysis from normal cells, cells from similarly diseased tissue, and the like, can provide an indication of the disease staging. A database of reference differential progenitor analyses can be compiled. An analysis of particular interest tracks a patient, e.g. in the chronic and pre-leukemic stages of disease, such that acceleration of disease is observed at an early stage. The methods of the invention provide detection of acceleration prior to onset of clinical symptoms, and therefore allow early therapeutic intervention, e.g. initiation of chemotherapy, increase of chemotherapy dose, changing selection of chemotherapeutic drug, and the like.

Tumor Classification and Patient Stratification.

Methods are also provided for optimizing therapy, by first classification, and based on that information, selecting the appropriate therapy, dose, treatment modality, etc. which optimizes the differential between delivery of an anti-proliferative treatment to the undesirable target cells, while minimizing undesirable toxicity. The treatment is optimized by selection for a treatment that minimizes undesirable toxicity, while providing for effective anti-proliferative activity.

In one aspect, the disclosure provides for methods of classifying lesions, e.g. tumor lesions, immune disorder samples, and the like, and thus grouping or "stratifying" patients, according to the single cell (including CSC) gene expression signature. For example, tumors classified as having a high percentage of cancer stem cells carry a higher risk of metastasis and death, and therefore may be treated more aggressively than tumors of a more benign type. Thus, analysis of populations or subpopulations present in a patient sample can be utilized to characterize the status of a disease, monitor treatment regimens and/or develop therapeutic approaches.

The sample of each patient in a pool of potential patients for a clinical trial can be classified as described above. Patients having similarly classified lesions can then be selected for participation in an investigative or clinical trial of a therapeutic where a homogeneous patient population is desired. The classification of a patient can also be used in assessing the efficacy of a therapeutic in a heterogeneous patient population. Thus, comparison of an individual's expression profile to the population profile for disease classification permits the selection or design of drugs or other therapeutic regimens that are expected to be safe and efficacious for a particular patient or patient population (i.e., a group of patients having the same type of cancer). Classification can be based on the expression (or lack thereof) of 1, 2, 3, 4, 5, 6, 7, 8, 9, 10, 11, 12, 13, 14, 15, 16, 17, 18, 19, 20, 25, 30, 35, 40, 45, 50 or more nucleic acids and/or proteins.

Diagnosis, Prognosis, Assessment of Therapy (Therametrics), and Management of Disorders The classification methods described herein, as well as their gene products and corresponding genes and gene products, are of particular interest as genetic or biochemical markers (e.g., in blood or tissues) that will detect the earliest changes along a disease pathway (e.g., a carcinogenesis pathway, inflammatory pathway, etc.), and/or to monitor the efficacy of various therapies and preventive interventions.

Staging is a process used by physicians to describe how advanced the cancerous state is in a patient. Staging assists the physician in determining a prognosis, planning treatment and evaluating the results of such treatment. Staging systems vary with the types of cancer, but generally involve the following "TNM" system: the type of tumor, indicated by T; whether the cancer has metastasized to nearby lymph nodes, indicated by N; and whether the cancer has metastasized to more distant parts of the body, indicated by M. Generally, if a cancer is only detectable in the area of the primary lesion without having spread to any lymph nodes it is called Stage I. If it has spread only to the closest lymph nodes, it is called Stage II. In Stage III, the cancer has generally spread to the lymph nodes in near proximity to the site of the primary lesion. Cancers that have spread to a distant part of the body, such as the liver, bone; brain or other site, are Stage IV, the most advanced stage.

The methods described herein can facilitate fine-tuning of the staging process by identifying the aggressiveness of a cancer, e.g. the metastatic potential, as well as the presence in different areas of the body. Thus, a Stage II cancer with a classification signifying a high metastatic potential cancer can be used to change a borderline Stage II tumor to a Stage III tumor, justifying more aggressive therapy. Conversely, the presence of a polynucleotide signifying a lower metastatic potential allows more conservative staging of a tumor.

For example, a breast cancer biopsy from a Stage II patient is analyzed by the methods described herein. The breast cancer may be classified as having a high metastatic potential depending upon the expression profile(s) determined from a patient's cells. Thus, a treating physician may use such information to more aggressively treat the patient than he or she would without the further classification. Determination of the expression of particular markers can also provide information on potential targets for drug therapy (e.g., tumorigenic cells from a patient expressing a drug target).

Development and Identification of Therapeutics.

The methods and compositions described herein can be utilized for the development or identification of new therapeutic agents and/or refining of existing therapies. For example, using single-cell analysis, expression profiles for target cell populations (e.g., cancer stem cells, cancer stem cells and differentiated cancer cells, or differentiated cancer cells) can be analyzed to detect potential targets for therapeutic agents. Potential targets include, without limitation, particular biomarkers and mis-regulated pathways. Targets of interest can include markers or pathways specific to the cell population(s) of interest.

In one instance, cells of a target population or subpopulation can be analyzed for expression of nucleic acids as described herein to detect novel biomarkers which can be targeted for treatment. For example, a particular cell surface molecule expressed exclusively in cancer stem cells and/or differentiated cancer cells can be investigated as a target for a potential therapeutic agent (e.g., an antibody or other binding moiety—potentially conjugated with a toxin or other such effector—with specificity for the surface molecule). In other instances, target cell populations can be analyzed for mis-regulation of pathways involved in disease processes (e.g., loss of control of cell-cycling machinery in cancer cells). Pathways can include, without limitation, activators and/or repressors of gene expression, expression of particular genes or sets of genes, and more complex, global pathways. Therapeutic agents that target such mis-regulation can potentially affect target cells to alter expression of nucleic acids associated with the target cells. Altered expression induced by therapeutic agents can result in up- or down-regulation of the nucleic acid. In some instances, treatment of cells and/or a subject with one or more therapeutic agents can result in expression of nucleic acids which imitates the expression in non-disease-state cells (e.g., treatment results in expression of cell-cycle related genes similar to that of non-cancerous cells).

Using the methods and compositions described herein, target cell populations can be analyzed for altered expression of one or more nucleic acids. The development of new and/or refined therapeutic agents can involve analyzing a target cell population (e.g., colon cancer stem cells, breast cancer cells, etc.) to determine nucleic acids which exhibit altered expression profiles as compared to "normal" cells. Such cells can be utilized to screen potential therapeutic agents for effect(s) on expression of these and/or other nucleic acids by exposing isolated cells of the target population to candidate agents and testing for altered expression of the genes following exposure.

The methods disclosed herein can also be utilized to analyze the effects of compounds which affect certain cellular phenotypes, including but not limited to, gene expression, pathway functioning (e.g., cell cycling, TERT pathway, oxidative stress pathways), and or cell type or morphology. Thus, compounds which affect such phenotypic characteristics can be analyzed in addition to or in lieu of analyzing a compound's potential as a therapeutic agent. For example, analysis of changes in gene expression in a target population (e.g., normal colon cells, normal breast cells, cancer cells, stem cells, cancer stem cells, etc.) exposed to one or more test compounds can performed to analyze the effect(s) of the test compounds on gene expression or other desired phenotypes (e.g., marker expression, cell viability). Such analyses can be useful for multiple purposes, for example cell cycle research or analysis of known or unknown pathways.

Agents to be analyzed for potential therapeutic value can be any compound, small molecule, protein, lipid, carbohydrate, nucleic acid or other agent appropriate for therapeutic use. Isolated cells of a target population can be exposed to libraries of potential therapeutic agents (e.g., antibody libraries, small molecule libraries) to determine effects on gene expression and/or cell viability. In some instances a candidate therapeutic agent will specifically target the cell population of interest. For example, upon single-cell analysis the existence of a mutation which is present in target cells (e.g., cancer stem cells and/or differentiated cancer cells) is revealed, a candidate therapeutic agent can target the mutation. In some instances, treated cells can be exposed to single-cell analysis to determine effects of the candidate therapeutic agent(s) on the expression of one or more genes of interest and/or effects on the transcriptome.

In other embodiments of the invention, agents are targeted to a disease-state cell population or subpopulation by specific binding to a marker or combination of markers present on the target population or subpopulation. In some embodiments, the agents include antibodies or antigen-binding derivatives thereof specific for a marker or combination of markers, which are optionally conjugated to a cytotoxic moiety. Such approaches can be used to deplete the target population or subpopulation in a patient (e.g., deplete cancer stem cell populations).

Therapeutic Agent Screening Assays

Cells (e.g., disease-state cells) expressing a marker or combination of markers are also useful for in vitro assays and screening to detect factors and chemotherapeutic agents that are active on differentiated cancer cells and/or cancer stem cells. Of particular interest are screening assays for agents that are active on human cells. A wide variety of assays may be used for this purpose; including immunoassays for protein binding; determination of cell growth, differentiation and functional activity; production of factors; and the like (see, e.g., Balis, (2002) *J. Nat'l Cancer Inst.* 94:2; 78). In other embodiments, isolated polypeptides corresponding to a marker or combination of markers of the present invention are useful in drug screening assays.

In screening assays for biologically active agents, anti-proliferative drugs, etc. a marker or a target cell composition is contacted with the agent of interest, and the effect of the agent assessed by monitoring output parameters on cells, such as expression of markers, cell viability, and the like; or binding efficacy or effect on enzymatic or receptor activity for polypeptides. For example, a breast cancer cell composition known to have a "cancer stem cell" expression profile is exposed to a test agent and exposed cells are individually analyzed as described herein to determine whether the test agent altered the expression profile as compared to non-treated cells. Any isolated cell population described herein or produced by the methods described herein may be freshly isolated, cultured, genetically altered, and the like. The cells can be environmentally induced variants of clonal cultures: e.g., split into independent cultures and grown under distinct conditions, for example with or without drugs; in the presence or absence of cytokines or combinations thereof. The manner in which cells respond to an agent (e.g., a peptide, siRNA, small molecule, etc.), particularly a pharmacologic agent, including the timing of responses, is an important reflection of the physiologic state of the cell.

Parameters are quantifiable components of cells, particularly components that can be accurately measured, for instance in a high throughput system. A parameter can be any cell component or cell product including cell surface determinant, receptor, protein or conformational or posttranslational modification thereof, lipid, carbohydrate, organic or inorganic molecule, nucleic acid, e.g. mRNA, DNA, etc. or a portion derived from such a cell component or combinations thereof. For example, in one embodiment, isolated cells as described herein are contacted with one or more agents and the level of expression of a nucleic acid of interest is determined. Agents which alter the expression of the detected nucleic acid(s), e.g., where the cells exhibit an expression pattern more similar to a non-disease state cell, can be further analyzed for therapeutic potential. While most parameters (e.g., mRNA or protein expression) will provide a quantitative readout, in some instances a semi-quantitative or qualitative result is acceptable. Readouts may include a single determined value, or may include mean, median value or the variance, etc. Characteristically a range of parameter readout values is obtained for each parameter from a multiplicity of the same assays. Variability is expected and a range of values for each of the set of test parameters are obtained using standard statistical methods with a common statistical method used to provide single values.

Agents of interest for screening include known and unknown compounds that encompass numerous chemical classes, primarily organic molecules, which may include organometallic molecules, genetic sequences, etc. An important aspect of the invention is to evaluate candidate drugs, including toxicity testing; and the like.

In addition to complex biological agents candidate agents include organic molecules comprising functional groups necessary for structural interactions, particularly hydrogen bonding, and typically include at least an amine, carbonyl, hydroxyl or carboxyl group, frequently at least two of the functional chemical groups. The candidate agents can comprise cyclical carbon or heterocyclic structures and/or aromatic or polyaromatic structures substituted with one or more of the above functional groups. Candidate agents can also be found among biomolecules, including peptides, polynucleotides, saccharides, fatty acids, steroids, purines, pyrimidines, derivatives, structural analogs or combinations thereof. In some instances, test compounds may have known functions (e.g., relief of oxidative stress), but may act through an unknown mechanism or act on an unknown target.

Included are pharmacologically active drugs, genetically active molecules, etc. Compounds of interest include chemotherapeutic agents, hormones or hormone antagonists, etc. Exemplary of pharmaceutical agents suitable for this invention are those described in, "The Pharmacological Basis of Therapeutics," Goodman and Gilman, McGraw-Hill, New York, N.Y., (1996), Ninth edition, under the sections: Water, Salts and Ions; Drugs Affecting Renal Function and Electrolyte Metabolism; Drugs Affecting Gastrointestinal Function; Chemotherapy of Microbial Diseases; Chemotherapy of Neoplastic Diseases; Drugs Acting on Blood-Forming organs; Hormones and Hormone Antagonists; Vitamins, Dermatology; and Toxicology, all incorporated herein by reference. Also included are toxins, and biological and chemical warfare agents, for example see Somani, S. M. (Ed.), "Chemical Warfare Agents," Academic Press, New York, 1992).

Test compounds include all of the classes of molecules described above, and can further comprise samples of unknown content. Of interest are complex mixtures of naturally occurring compounds derived from natural sources such as plants, fungi, bacteria, protists or animals. While many samples will comprise compounds in solution, solid samples that can be dissolved in a suitable solvent may also be assayed. Samples of interest include environmental samples, e.g., ground water, sea water, mining waste, etc., biological samples, e.g. lysates prepared from crops, tissue samples, etc.; manufacturing samples, e.g. time course during preparation of pharmaceuticals; as well as libraries of compounds prepared for analysis; and the like (e.g., compounds being assessed for potential therapeutic value, i.e., drug candidates).

Samples or compounds can also include additional components, for example components that affect the ionic strength, pH, total protein concentration, etc. In addition, the samples may be treated to achieve at least partial fractionation or concentration. Biological samples may be stored if care is taken to reduce degradation of the compound, e.g. under nitrogen, frozen, or a combination thereof. The volume of sample used is sufficient to allow for measurable detection, for example from about 0.1 ml to 1 ml of a biological sample can be sufficient.

Compounds, including candidate agents, are obtained from a wide variety of sources including libraries of synthetic or natural compounds. For example, numerous means are available for random and directed synthesis of a wide variety of organic compounds, including biomolecules, including expression of randomized oligonucleotides and oligopeptides. Alternatively, libraries of natural compounds in the form of bacterial, fungal, plant and animal extracts are available or readily produced. Additionally, natural or synthetically produced libraries and compounds are readily modified through conventional chemical, physical and biochemical means, and may be used to produce combinatorial libraries. Known pharmacological agents may be subjected to directed or random chemical modifications, such as acylation, alkylation, esterification, amidification, etc. to produce structural analogs.

Agents are screened for biological activity by adding the agent to at least one and usually a plurality of cell samples, usually in conjunction with cells lacking the agent. The change in parameters in response to the agent is measured, and the result evaluated by comparison to reference cultures, e.g. in the presence and absence of the agent, obtained with other agents, etc:

The agents can be added in solution, or readily soluble form, to the medium of cells in culture. The agents may be added in a flow-through system, as a stream, intermittent or continuous, or alternatively, adding a bolus of the compound, singly or incrementally, to an otherwise static solution. In a flow-through system, two fluids are used, where one is a physiologically neutral solution, and the other is the same solution with the test compound added. The first fluid is passed over the cells, followed by the second. In a single solution method, a bolus of the test compound is added to the volume of medium surrounding the cells. The overall concentrations of the components of the culture medium should not change significantly with the addition of the bolus, or between the two solutions in a flow through method.

Some agent formulations do not include additional components, such as preservatives, that may have a significant effect on the overall formulation. Thus, such formulations consist essentially of a biologically active compound and a physiologically acceptable carrier, e.g. water, ethanol, DMSO, etc. However, if a compound is liquid without a solvent, the formulation may consist essentially of the compound itself.

A plurality of assays may be run in parallel with different agent concentrations to obtain a differential response to the various concentrations. As, known in the art, determining the effective concentration of an agent typically uses a range of concentrations resulting from 1:10, or other log scale, dilutions. The concentrations may be further refined with a second series of dilutions, if necessary. Typically, one of these concentrations serves as a negative control, i.e. at zero concentration or below the level of detection of the agent or at or below the concentration of agent that does not give a detectable change in the phenotype.

Various methods can be utilized for quantifying the presence of the selected markers. For measuring the amount of a molecule that is present, a convenient method is to label a molecule with a detectable moiety, which may be fluorescent, luminescent, radioactive, enzymatically active, etc., particularly a molecule specific for binding to the parameter with high affinity. Fluorescent moieties are readily available for labeling virtually any biomolecule, structure, or cell type.

Immunofluorescent moieties can be directed to bind not only to specific proteins but also specific conformations, cleavage products, or site modifications like phosphorylation. Individual peptides and proteins can be engineered to autofluoresce, e.g. by expressing them as green fluorescent protein chimeras inside cells (for a review see Jones et. al. (1999) Trends Biotechnol. 17(12):477-81). Thus, antibodies can be genetically modified to provide a fluorescent dye as part of their structure. Depending upon the label chosen, parameters may be measured using other than fluorescent labels, using such immunoassay techniques as radioimmunoassay (RIA) or enzyme linked immunosorbance assay (ELISA), homogeneous enzyme immunoassays, and related non-enzymatic techniques. The quantitation of nucleic acids, especially messenger RNAs, is also of interest as a parameter. These can be measured by hybridization techniques that depend on the sequence of nucleic acid nucleotides. Techniques include polymerase chain reaction methods as well as gene array techniques. See Current Protocols in Molecular Biology, Ausubel et al., eds, John Wiley & Sons, New York, N.Y., 2000; Freeman at al. (1999) Biotechniques 26(1):112-225; Kawamoto at al. (1999) Genome Res 9(12):1305-12; and Chen et al. (1998) Genomics 51(3):313-24, for examples.

Databases of Expression Profiles and Data Analysis

Also provided are databases of gene expression profiles of cancer stem cells and other cell types and uses thereof. Such databases will typically comprise expression profiles derived from various cell subpopulations, such as cancer stem cells, cancer non-stem cells, normal counterparts to cancer cells, disease-state cells (e.g., inflammatory bowel cells, ulcerative colitis cells), virally infected cells, early progenitor cells, initially differentiated progenitor cells, late differentiated progenitor cells, and mature cells. The expression profiles and databases thereof may be provided in a variety of media to facilitate their use. "Media" refers to a manufacture that contains the expression profile information of the present invention. The databases of the present invention can be recorded on computer readable media, e.g. any medium that can be read and accessed directly by a computer. Such media include, but are not limited to: magnetic storage media, such as floppy discs, hard disc storage medium, and magnetic tape; optical storage media such as CD-ROM; electrical storage media such as RAM and ROM; and hybrids of these categories such as magnetic/optical storage media. One of skill in the art can readily appreciate how any of the presently known computer readable mediums can be used to create a manufacture comprising a recording of the present database information. "Recorded" refers to a process for storing information on computer readable medium, using any such methods as known in the art. Any convenient data storage structure may be chosen, based on the means used to access the stored information. A variety of data processor programs and formats can be used for storage, e.g. word processing text file, database format, etc.

As used herein, "a computer-based system" refers to the hardware means, software means, and data storage means used to analyze the information of the present invention. The minimum hardware of the computer-based systems of the present invention comprises a central processing unit (CPU), input means, output means, and data storage means. A skilled artisan can readily appreciate that any one of the currently available computer-based system are suitable for use in the present invention. The data storage means may comprise any manufacture comprising a recording of the present information as described above, or a memory access means that can access such a manufacture.

A variety of structural formats for the input and output means can be used to input and output the information in the computer-based systems of the present invention. Such presentation provides a skilled artisan with a ranking of similarities and identifies the degree of similarity contained in the test expression profile.

Various methods for analysis of a set of data may be utilized. In one embodiment, expression data is subjected to transformation and normalization. For example, ratios are generated by mean centering the expression data for each gene (by dividing the intensity measurement for each gene on a given array by the average intensity of the gene across all arrays), (2) then log-transformed (base 2) the resulting ratios, and (3) then median centered the expression data across arrays then across genes.

For cDNA microarray data, genes with fluorescent hybridization signals at least 1.5-fold greater than the local background fluorescent signal in the reference channel are considered adequately measured. The genes are centered by mean value within each dataset, and average linkage clustering carried out.

A scaled approach may also be taken to the data analysis. For example, Pearson correlation of the expression values of genes can provide a quantitative score reflecting the signature for each CSC. The higher the correlation value, the more the sample resembles a reference CSC phenotype. Similar correlation can be done for any cell type, including normal cells, progenitor cells, autoimmune phenotype cells, inflammatory phenotype cells, infected cells, differentiated cancer cells, normal stem cells, normal mature cells, etc. A negative correlation value indicates the opposite behavior. The threshold for the classification can be moved up or down from zero depending on the clinical goal. For example, sensitivity and specificity for predicting metastasis as the first recurrence event can be calculated for every threshold between −1 and +1 for the correlation score in 0.05 increments, and the threshold value giving a desired sensitivity, e.g. 80%, 90%, 95%, etc. for metastasis prediction can be selected.

To provide significance ordering, the false discovery rate (FDR) may be determined. First, a set of null distributions of dissimilarity values is generated. In one embodiment, the values of observed profiles are permuted to create a sequence of distributions of correlation coefficients obtained out of chance, thereby creating an appropriate set of null distributions of correlation coefficients (see Tusher et al. (2001) PNAS 98, 5118-21, herein incorporated by reference). The set of null distribution is obtained by: permuting the values of each profile for all available profiles; calculating the pairwise correlation coefficients for all profile; calculating the probability density function of the correlation coefficients for this permutation; and repeating the procedure for N times, where N is a large number, usually 300. Using the N distributions, one calculates an appropriate measure (mean, median, etc.) of the count of correlation coefficient values that their values exceed the value (of similarity) that is obtained from the distribution of experimentally observed similarity values at given significance level.

The FDR is the ratio of the number of the expected falsely significant correlations (estimated from the correlations greater than this selected Pearson correlation in the set of randomized data) to the number of correlations greater than this selected Pearson correlation in the empirical data (significant correlations). This cut-off correlation value may be applied to the correlations between experimental profiles.

Using the aforementioned distribution, a level of confidence is chosen for significance. This is used to determine the lowest value of the correlation coefficient that exceeds the result that would have obtained by chance. Using this method, one obtains thresholds for positive correlation, negative correlation or both. Using this threshold(s), the user can filter the observed values of the pairwise correlation coefficients and eliminate those that do not exceed the threshold(s). Furthermore, an estimate of the false positive rate can be obtained for a given threshold. For each of the individual "random correlation" distributions, one can find how many observations fall outside the threshold range. This procedure provides a sequence of counts. The mean and the standard deviation of the sequence provide the average number of potential false positives and its standard deviation.

The data can be subjected to non-supervised hierarchical clustering to reveal relationships among profiles. For example, hierarchical clustering may be performed, where the Pearson correlation is employed as the clustering metric. Clustering of the correlation matrix, e.g. using multidimensional scaling, enhances the visualization of functional homology similarities and dissimilarities. Multidimensional scaling (MDS) can be applied in one, two or three dimensions.

The analysis may be implemented in hardware or software, or a combination of both. In one embodiment of the invention, a machine-readable storage medium is provided, the medium comprising a data storage material encoded with machine readable data which, when using a machine programmed with instructions for using said data, is capable of displaying a any of the datasets and data comparisons of this invention. Such data may be used for a variety of purposes, such as drug discovery, analysis of interactions between cellular components, and the like. In some embodiments, the invention is implemented in computer programs executing on programmable computers, comprising a processor, a data storage system (including volatile and non-volatile memory and/or storage elements), at least one input device, and at least one output device. Program code is applied to input data to perform the functions described above and generate output information. The output information is applied to one or more output devices, in known fashion. The computer may be, for example, a personal computer, microcomputer, or work station of conventional design.

Each program can be implemented in a high level procedural or object oriented programming language to communicate with a computer system. However, the programs can be implemented in assembly or machine language, if desired. In any case, the language may be a compiled or interpreted language. Each such computer program can be stored on a storage media or device (e.g., ROM or magnetic diskette) readable by a general or special purpose programmable computer, for configuring and operating the computer when the storage media or device is read by the computer to perform the procedures described herein. The system may also be considered to be implemented as a computer-readable storage medium, configured with a computer program, where the storage medium so configured causes a computer to operate in a specific and predefined manner to perform the functions described herein.

A variety of structural formats for the input and output means can be used to input and output the information in the computer-based systems of the present invention. One format for an output means tests datasets possessing varying degrees of similarity to a trusted profile. Such presentation provides a skilled artisan with a ranking of similarities and identifies the degree of similarity contained in the test pattern.

Storing and Transmission of Data

Further provided herein is a method of storing and/or transmitting, via computer, sequence, and other, data collected by the methods disclosed herein. Any computer or computer accessory including, but not limited to software and storage devices, can be utilized to practice the present invention. Sequence or other data (e.g., transcriptome data), can be input into a computer by a user either directly or indirectly: Additionally, any of the devices which can be used to sequence DNA or analyze DNA or analyze transcriptome data can be linked to a computer, such that the data is transferred to a computer and/or computer-compatible storage device. Data can be stored on a computer or suitable storage device (e.g., CD). Data can also be sent from a computer to another computer or data collection point via methods well known in the art (e.g., the internet, ground mail, air mail). Thus, data collected by the methods described herein can be collected at any point or geographical location and sent to any other geographical location.

Figure 10:
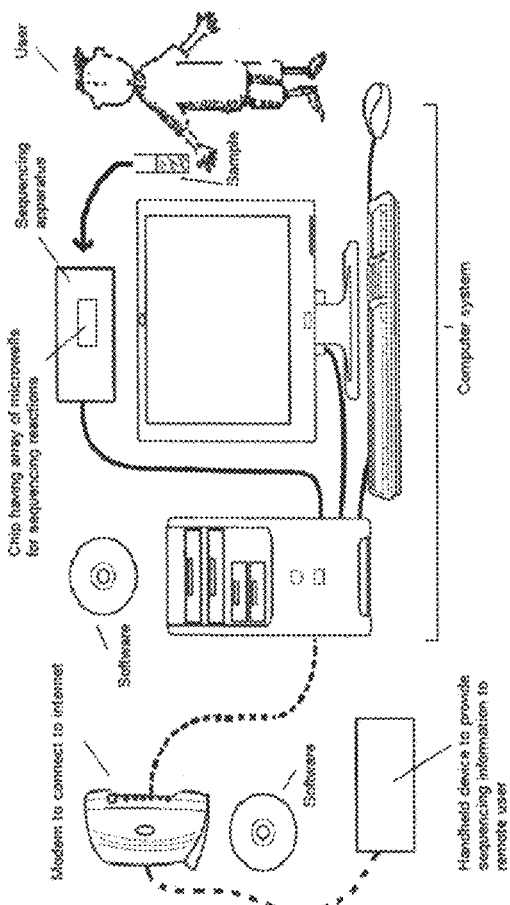
FIG. 10. A pictorial representation of data collection, storage and transport via computer.

An exemplary method is illustrated in FIG. 10. In this example, a user provides a sample into a sequencing apparatus. Data is collected and/or analyzed by the sequencing apparatus which is connected to a computer. Software on the computer allows for data collection and/or analysis. Data can be stored, displayed (via a monitor or other similar device), and/or sent to another location. As shown in FIG. 10, the computer is connected to the internet which is utilized to transmit data to a handheld device utilized by a remote user (e.g., a physician, scientist or analyst). It is understood that the data can be stored and/or analyzed prior to transmittal. In some embodiments, raw data can be collected and sent to a remote user who will analyze and/or store the data: Transmittal can occur, as shown in FIG. 10, via the internet, but can also occur via satellite or other connection. Alternately, data can be stored on a computer-readable medium (e.g., CD, memory storage device) and the medium can be shipped to an end user (e.g., via mail). The remote user can be in the same or a different geographical location including, but not limited to a building, city, state, country or continent.

Reagents and Kits

Also provided are reagents and kits thereof for practicing one or more of the above-described methods. The subject reagents and kits thereof may vary greatly. Reagents of interest include reagents specifically designed for use in production of the above described expression profiles of phenotype determinative genes. For example, reagents can include primer sets for genes known to be differentially expressed in a target population or subpopulation (e.g., reagents for detecting tumorigenic breast cancer cells can include primers and probes for expanding and detecting expression of CD49f, CD24, and/or EPCAM).

One type of reagent that is specifically tailored for generating expression profiles of target cell populations and subpopulations is a collection of gene specific primers that is designed to selectively amplify such genes, for use in quantitative PCR and other quantitation methods. Gene specific primers and methods for using the same are described in U.S. Pat. No. 5,994,076, the disclosure of which is herein incorporated by reference. Of particular interest are collections of gene specific primers that have primers for at least 5 of genes, often a plurality of these genes, e.g., at least 10, 15, 20, 30, 40, 50, 60, 70, 80, 90, 100, 200, 300, 400, 500, 600, 700, 800, 900, 1000 genes or more. The gene specific primer collections can include only primers for genes associated with a target population or subpopulation (e.g., mutations, known mis-regulated genes, etc.), or they may include primers for additional genes (e.g., housekeeping genes, controls).

The kits of the subject invention can include the above described gene specific primer collections. The kits can further include a software package for statistical analysis of one or more phenotypes, and may include a reference database for calculating the probability of susceptibility. The kit may include reagents employed in the various methods, such as primers for generating target nucleic acids, dNTPs and/or rNTPs, which may be either premixed or separate, one or more uniquely labeled dNTPs and/or rNTPs, such as biotinylated or Cy3 or Cy5 tagged dNTPs, gold or silver particles with different scattering spectra, or other post synthesis labeling reagent, such as chemically active derivatives of fluorescent dyes, enzymes, such as reverse transcriptases, DNA polymerases, RNA polymerases, and the like, various buffer mediums, e.g. hybridization and washing buffers, prefabricated probe arrays, labeled probe purification reagents and components, like spin columns, etc., signal generation and detection reagents, e.g. streptavidin-alkaline phosphatase conjugate, chemifluorescent or chemiluminescent substrate, and the like.

In addition to the above components, the subject kits will further include instructions for practicing the subject methods. These instructions may be present in the subject kits in a variety of forms, one or more of which may be present in the kit. One form in which these instructions may be present is as printed information on a suitable medium or substrate, e.g., a piece or pieces of paper on which the information is printed, in the packaging of the kit, in a package insert, etc. Yet another means would be a computer readable medium, e.g., diskette, CD, etc., on which the information has been recorded. Yet another means that may be present is a website address which may be used via the internet to access the information at a removed, site. Any convenient means may be present in the kits.

The above-described analytical methods may be embodied as a program of instructions executable by computer to perform the different aspects of the invention. Any of the techniques described above may be performed by means of software components loaded into a computer or other information appliance or digital device. When so enabled, the computer, appliance or device may then perform the above-described techniques to assist the analysis of sets of values associated with a plurality of genes in the manner described above, or for comparing such associated values. The software component may be loaded from a fixed media or accessed through a communication medium such as the internet or other type of computer network. The above features are embodied in one or more computer programs may be performed by one or more computers running such programs.

EXAMPLES

The following examples are offered by way of illustration and not by way of limitation.

Example 1

Analysis of Gene Expression in Single Cells

A significant fraction of murine breast CSCs contain relatively low levels of ROS, and so it was hypothesized that these cells may express enhanced levels of ROS defenses compared to their NTC counterparts.

Single Cell Gene Expression Analysis.

For the single cell gene expression experiments we used qPCR DynamicArray microfluidic chips (Fluidigm). Single MMTV-Wnt-1 Thy1$^+$CD24$^+$Lin-CSC-enriched cells (TG) and "Not Thy1$^+$CD24$^+$"Lin" non-tumorigenic (NTG) cells were sorted by FACS into 96 well plates containing PCR mix (CellsDirect, Invitrogen) and RNase Inhibitor (Superaseln, Invitrogen). After hypotonic lysis we added RT-qPCR enzymes (SuperScript III RT/Platinum Taq, Invitrogen), and a mixture containing a pool of low concentration assays (primers/probes) for the genes of interest (Gclm-Mm00514996_m1, Gss-Mm00515065_m1, Foxo1-Mm00490672_m1, Foxo4-Mm00840140_g1, H ifla Mm00468875_m1, Epas1-Mm00438717_m1). Reverse transcription (15 minutes at 50° C., 2 minutes of 95° C.) was followed by pre-amplification for 22 PCR cycles (each cycle: 15 sec at 95° C., 4 minutes at 60° C.). Total RNA controls were run in parallel. The resulting amplified cDNA from each one of the cells was inserted into the chip sample inlets with Taqman qPCR mix (Applied Biosystems). Individual assays (primers/probes) were inserted into the chip assay inlets (2 replicates for each). The chip was loaded for one hour in a chip loader (Nanoflex, Fluidigm) and then transferred to a reader (Biomark, Fluidigm) for thermocycling and fluorescent quantification. To remove low quality gene assays, we discarded gene assays whose qPCR curves showed non-exponential increases. To remove low quality cells (e.g. dead cells) we discarded cells that did not express the housekeeping genes Actb (beta-actin) and Hprt1 (hypoxanthine guanine phosphoribosyl transferase 1). This resulted in a single cell gene expression dataset consisting of 248 cells (109 tumorigenic and 139 non-tumorigenic) from a total of 7 chip-runs. A two sample Kolmogorov-Smirnov (K-S) statistic was calculated to test if genes were differentially expressed in the two populations. We generated p values by permuting the sample labels (i.e. TG vs NTG) and comparing the actual K-S statistic to those in the permutation-derived null distribution. The p values were further corrected by Bonferroni correction to adjust for multiple hypothesis testing. EXAMPLE 2 Analysis and quantification of human "colorectal cancer stem cells" (Co-CSC) using SINCE-PCR, a novel method based on "single-cell gene expression analysis."

The SINCE-PCR method allows the identification, characterization and quantification of "cancer stem cells" in human colorectal cancer tissues, with a degree of purity and resolution that was previously not achievable. Cancer stem cells, which can be tumorigenic or tumor-initiating cells, are a subpopulation of cancer cells that can have the capacity to form tumors when transplanted in immunodeficient mice. Cancer stem cell populations have currently been identified in breast, brain, head & neck, pancreatic and colon cancer. Accurate functional definition and quantification of "cancer stem cells" has several important implications for diagnosis, prognosis, classification and therapeutic targeting of human, cancer.

We describe a novel method for the identification, analysis and quantification of "cancer stem cells" in human colorectal cancer tissues, based on single-cell gene expression analysis by real-time polymerase chain reaction (real-time PCR). We have identified a novel set of genes whose coordinated and differential expression can be used as a "signature" to identify distinct cancer cell subsets within the same tumor tissue. This novel set of genes includes housekeeping genes common to all epithelial cells (EpCAM, beta-Actin, GAPDH), genes related to stem-cell biology (hTERT, LGR5, Survivin) and genes involved in tissue-specific differentiation pathways related to the distinct cellular lineages (Carbonic Anhydrase II, MUC2, Trefoil Family Factor 3) and differentiation stages (Cytokeratin 20, CD66a/CEACAM1) of the normal colonic epithelium. Based on the expression pattern of this set of genes, epithelial cells purified from human colorectal cancer tissues and analyzed individually as single-cells can be "classified" and clustered in distinct groups, corresponding to more or less advanced stages of differentiation (e.g. terminally differentiated cells at the top of the human colonic crypt vs. more immature cells located at the bottom of the human colonic crypt) and to distinct differentiation lineages of the colonic epithelium (e.g. goblet cells, enterocytes, immature cells). Each group can be quantified as a percentage of the total population. We have named this approach and methodology for the analysis of the cellular composition of biological tissues "SINCE-PCR" (Single Cell Expression-Polymerase Chain Reaction).

Our discovery is based on several observations. Human "colorectal cancer stem cells" enriched by flow cytometry directly from freshly harvested solid tumor tissues can be reproducibly and robustly analyzed at the single-cell level (FIG. 1).

Figure 2B:
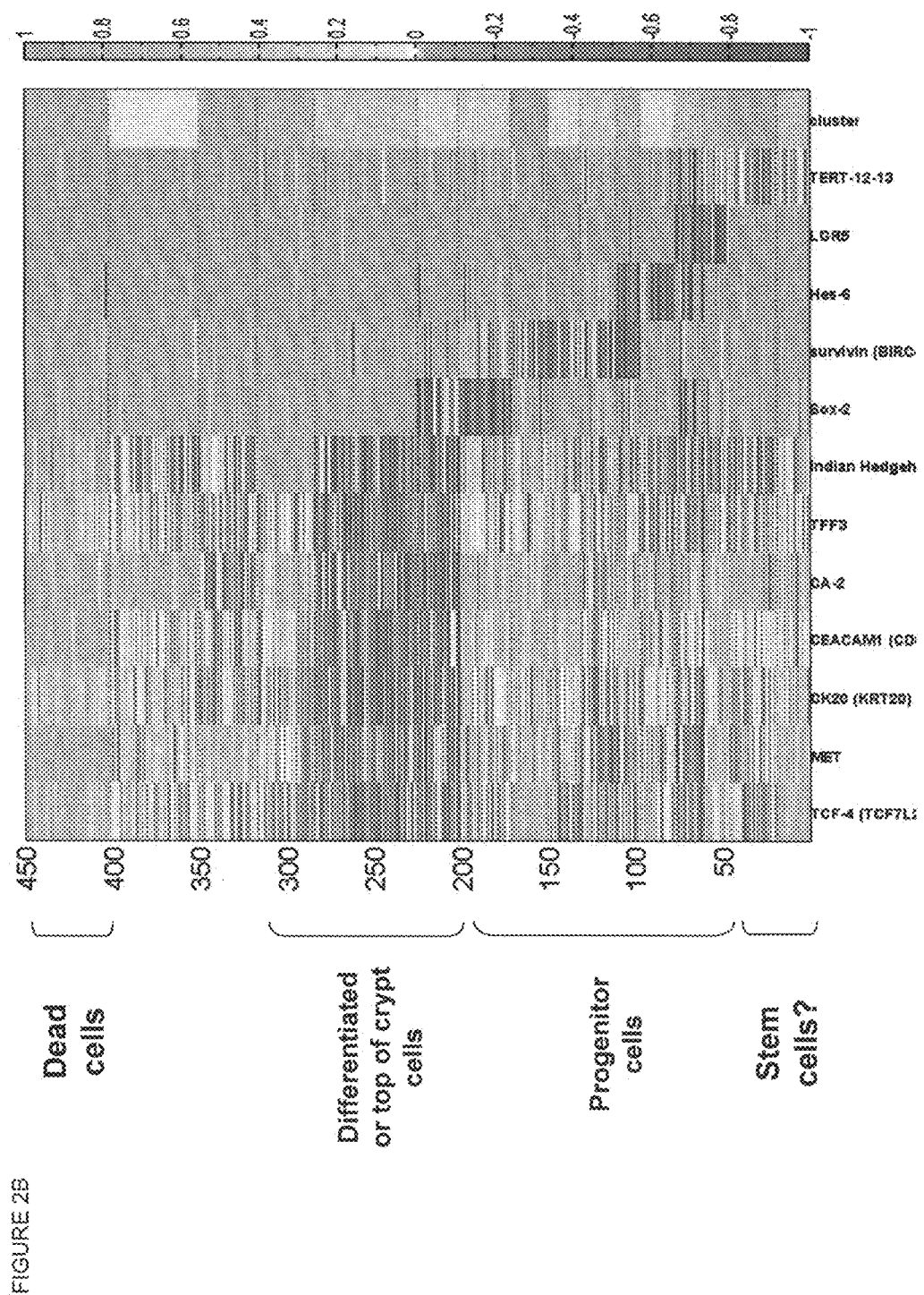
Figure 3:
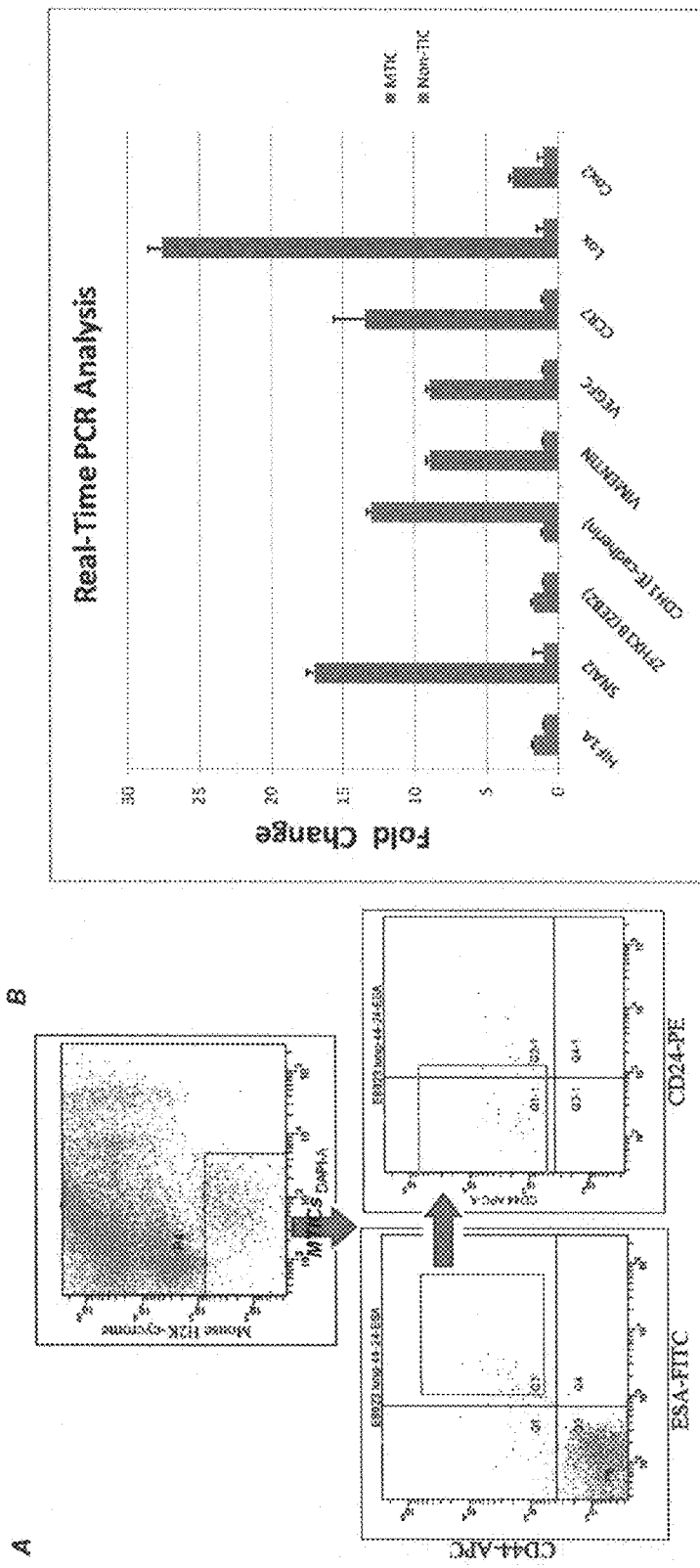
FIG. 3A-B. a: Purification of MTICs 11'ESA+H2K—from the lung cells of breast tumor-bearing NOD/SCID mice. Top panel gated H2K-Dapilviable lineage), lower left panel gated ESA+ cells for furthering gating of CD2441' cells in the lower right panel. b: Real time PCR analysis of mRNA levels of HIF1a, Snail2, Zeb2, E-cadherin, Vimentin, VEGFC, CCR7, Lox, Cox2 in MTIC and non-TICs.

In human colon cancer xenografts, single-cell gene expression analysis by real-time PCR indicates that both EpCAM-/CD44$^+$ and EpCAM-/VCD166$^+$ cancer cells, which are known to be enriched for the "colorectal cancer stem cell" population, can be further subdivided in different cellular subsets characterized by the coordinated and differential expression of distinct groups of genes involved in stem cell biology and differentiation processes. Most interestingly, cell subsets that display higher levels of genes encoding for known colonic epithelial terminal differentiation markers (e.g. Cytokeratin 20, CD66a/CEACAM1 Carbonic Anhydrase II, MUC2, Trefoil Family Factor 3) do not express or express lower levels of genes encoding for candidate intestinal stem cell markers or genes known to be necessary for stem cell function (e.g. hTERT, LGR5, Survivin) and vice-versa. This suggests that EpCAM/CD44$^+$/CD166$^+$ cancer cells contain distinct cellular subsets characterized by different stages of differentiation (FIG. 2).

When purified by means of fluorescence-activated cell sorting (FACS) and re-injected in immunodeficient NOD/SCID mice, CD44$^+$/CD66a$^+$ and CD44$^+$/CD66anew1" cells display substantially different tumorigenic properties, with the CD44$^+$/CD66a$^{neglow}$ population behaving as the one endowed with the highest tumorigenic capacity (Table 4). This indicates that, within the EpCAM$^+$/CD44$^+$ cell population, the cell subset that is characterized by high levels of expression of genes that encode for differentiation markers such as CD66a/CEACAMI (i.e the more "mature" cell subset) is frequently relatively depleted of tumorigenic capacity. On the other hand, the cell subset that is characterized by the absence or low levels of expression of differentiation markers such as CD66a/CEACAMI (i.e the more "immature" cell subset) is enriched in "colorectal cancer stem cell" content.

TABLE 1

Tumorigenic properties of human colon cancer cells based on CD66a/CEACAMI expression, in combination with EpCAM and/or CD44.

| Exp. | Tumor source$^a$ | | Lin$^{neg}$ sorted populations$^b$ | Cell dose | Tumor Take$^c$ | Experiment code |
|---|---|---|---|---|---|---|
| 1) | UM#4 | m4 | CD44$^{neg}$ | 10,000 | 2/10 | PD69- |
| | | | CD44$^+$/CD66a$^+$ | 450 | 1/3 | |
| | | | CD44$^+$/CD66a$^{neg-low}$ | 250 | 2/3 | |
| 2) | UM#4 | m6 | CD44$^{neg}$ | 10,000 | 1/5 | PD85 |
| | | | CD44$^+$/CD66a$^+$ | 500 | 0/2 | |
| | | | CD44$^+$/CD66a$^{neg-low}$ | 1,000 | 3/3 | |
| 3) | UM#4 | m4 | CD44$^{neg}$ | 10,000 | 0/5 | PD107 |
| | | | CD44$^+$/CD66a$^+$ | 1,000 | 0/1 | |
| | | | CD44$^+$/CD66a$^{neg-low}$ | 1,000 | 3/4 | |
| 4) | SU29 | m1 | CD44$^{neg}$ | 7,000 | 0/5 | PD88- |
| | | | CD44$^+$/CD66a$^+$ | 1,000 | 0/5 | |
| | | | CD44$^+$/CD66a$^{neg-low}$ | 2,000 | 1/5 | |
| | | — | " | 1,000 | 0/5 | |
| 5) | SU43 | primary | EpCAM$^+$/CD44$^{neg}$ | 12,000 | 0/5 | PD79 |
| | | | EpCAM$^+$/CD44$^+$/CD66a$^+$ | 300 | 0/1 | |
| | | | EpCAM$^+$/CD44$^+$/CD66a$^{neg-low}$ | 1,000 | 1/3 | |

$^a$For each experiment, the in vivo serial passage of the tumor xenograft used as source for cancer cell purification is reported as follows: m1 indicates the first round of tumors obtained from primary tumor engraftment, m2 the second round of tumors obtained from engraftment of m1, m3 the third round of tumors obtained from engraftment of m2, and so on progressively; primary indicates a primary tumor, directly harvested from a surgical specimen.
$^b$All sorted populations are to be considered as negative for lineage markers (Lin$^{neg}$), which include mouse CD45 and mouse H2-Kd in the case of human tumor xenografts established in NOD/SCID mice, and human CD3 and CD45 in the case of primary human tumors (in this case EpCAM serves as a positive epithelial selection marker)
$^c$Tumor take is reported as: number of tumors obtained/number of injections; tumor take is considered unsuccessful when no tumor mass is visible after 5 months follow-up.

Example 2

Generation and Imaging of Human Breast Cancer Xenograft Models with Pulmonary Metastases Patient-derived breast cancer specimens (chunks or TICs) were orthotopically transplanted into the mammary fat pads of NOD-SCID mice. Six xenograft tumor models were generated (1 ER$^+$, 1 Her2$^+$ and 4 triple negative ER-PR-Her2-). All four of the triple negative xenografts developed spontaneous lung micro-metastases, demonstrated by IHC stainings, i.e H&E, proliferation marker Ki67 and Vimentin (Vim) stainings. These data suggested that upon implantation into immunodeficient mice, breast tumor cells or TICs are able to adapt to the mouse microenvironment and recapitulate human tumor growth and progression with spontaneous lung metastasis.

To facilitate dynamic and semi-quantitative imaging of human breast cancer and metastasis in mice, the breast TICs were transduced with firefly luciferase-EGFP fusion gene via the pHRuKFG lentivirus (moi 50) 4 days after implantation, TICs at the primary site were detectable with weak bioluminescent signals. And one month later, both primary tumors (at the L4 and R2 mammary fat pads) and lung metastases were detected and imaged by Xenogen IVIS 200 system at the Small Animal Imaging Center of Stanford. We observed that tumor size or cell numbers correlated well with the signal intensity. The generation and bioluminescent imaging of xenograft tumors with metastasis provide us feasibility of validating functions of miRNAs in MTICs of human breast cancer in viva in this proposal.

Example 3

Microarray and Real-Time PCR Analysis of Human Breast MTICs

Human breast primary tumor initiating cells (TICs) or metastatic TICs (MTICs) (CD44$^+$CD24$^{-/low}$ESA$^+$lineage$^-$) were isolated from breast cancer primary site or pleural effusions. Once lung mets were detected in xenograft models, lungs were dissociated with blenzyme (Roche) and stained cells with mouse H2K and human CD44, CD24 and ESA for purifying MTIC populations (CD44$^+$CD24$^{-/low}$ESA$^+$H2K$^-$, FIG. 8a), which grow orthotopic tumors at a ratio of 5/8 with 200-1000 sorted cells, after transplanted into mouse mammary fat pads.

Shown by microarray analysis and real-time PCR, HIF1α and HIF1 regulated target genes were differentially expressed in MTICs compared to non-tumorigenic tumor cells, including Snail, Zeb2, Vimentin, E-cadherin, Lox, Cox2, VEGF, etc. (FIG. 8B). Co-localization of HIF1α, Vimentin and CD44 were confirmed by immunohistochemistry staining.

Example 4

MicroRNA Analysis

By microRNA screening, differential expression profiles of parental breast cancer stem cells and metastatic cancer cells isolated from the lungs were identified. For example, higher expression of miR-10a and lower levels of miR-490, miR-199a, etc in lung MTICs than that of primary breast TICs. As shown by triplicate real-time PCR in FIG. 4, comparison of mean CT values of lung MTICs versus primary TICs: miR-10a (−7.9), miR-490 ($^+$3.0) and miR-199a ($^+$12.9).

NR3 was used as an internal control. The data indicated that miR-10a was upregulated by up to 27'9 fold, and miR-199a downregulated by 212-9 fold in MTICs than primary TICs of breast cancer.

Example 5

CD66a as a Non-Tumorigenic Cancer Cell Marker of Breast Cancer

Figure 5:
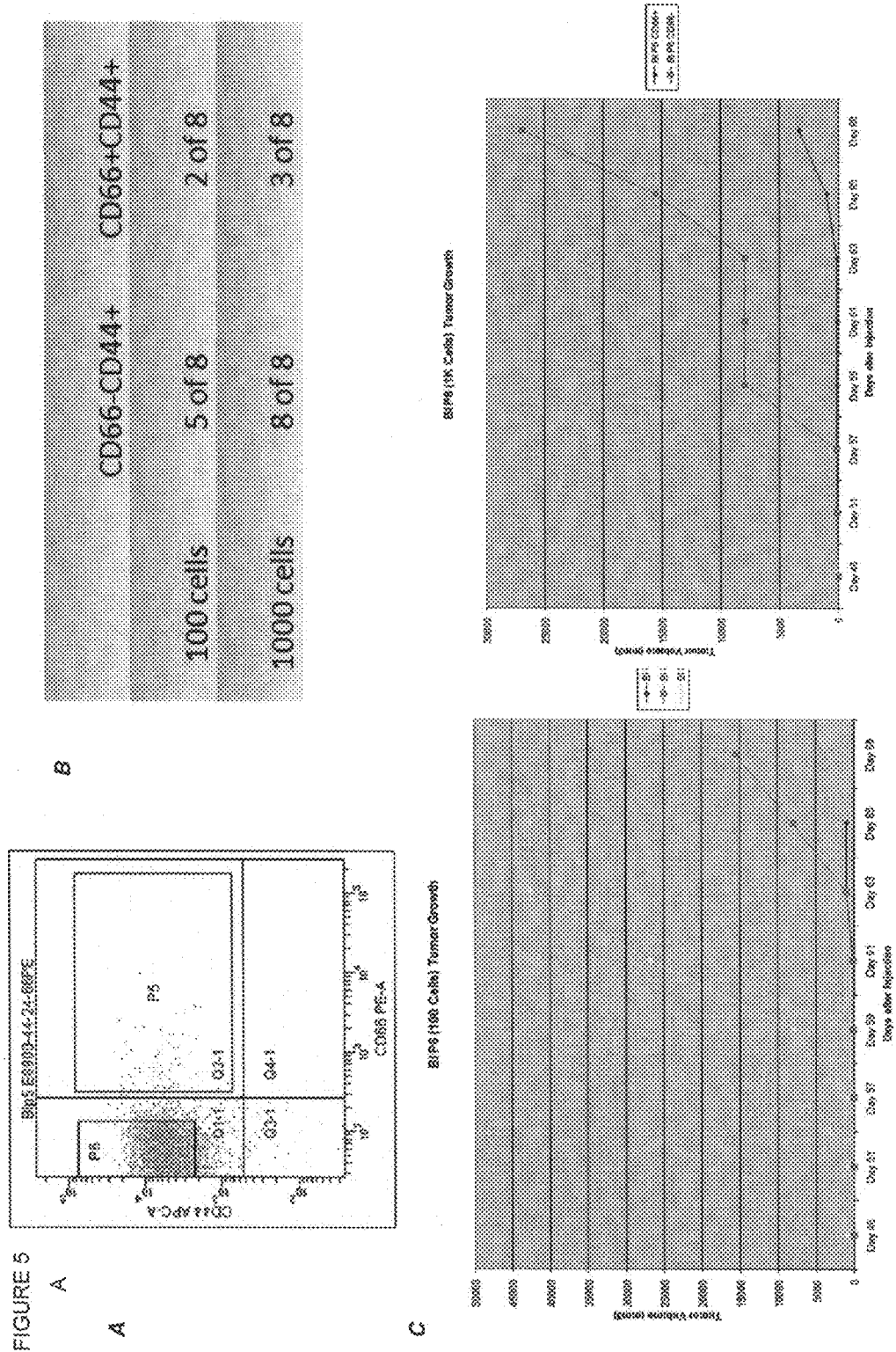
FIG. 5A-5D. CD66a as a non-tumorigenic cancer cell marker of breast cancer.

Breast cancer cells were sorted based on CD44 and CD66a while most of the cells were CD244bw. Cells were then implanted onto mammary fat pads of NOD/SCID mice and tumor growth monitored. CD44/CD66a-cells showed higher rate of transplantation as well as higher growth rate by bioluminescent imaging as shown in FIG. 5. $CD66^+$ cells showed a lower and delayed rate of tumor growth, the tumor size is much smaller and displayed very similar flow profiles compared to CD66-derived tumors.

In FIG. 5a, the flow profile was shown based on CD44 and CD66a markers. $CD66-CD44^+$ and $CD66^+CD44^+$ cells were sorted for in vivo tumorigenic assays (100 cells or 1000 cells implanted to Zid or 41 h of mammary fat pads of NOD/SLID mice). As 10b indicated, 5 of 8 implantations from 100 CD66-cells grew tumors while 2 of 8 from 100 $CD66^+$ cells grew. For 1000 cells, 8 of 8 from CD66-cell injections grew but only 3 of 8 from $CD66^+$ cells grew tumors. Comparing the growth rate of palpable tumors, $CD66^+$ cells had much lower and smaller sizes than those derived from CD66-cells (FIG. 5c). In FIG. 5d, 100K of $CD66-CD44^+$ or $CD66^+CD44^+$ cells were infected with firefly luciferase-EGFP lentivirus prior to injection. The bioluminescent signals from $CD66^+$ cells were higher than those of CD66-cells from the beginning (day 13). But after 1 month or 2 months, CD66-cells showed dominant bioluminescent signals and grew out palpable tumors in the end (day 68).

Example 6

Optimization of the Gene List Used to Identify and Measure Cancer Stem Cell Frequency Most markers used at this time to identify both normal stem cells and cancer stem cells are not linked to an essential stem cell function. Their expression is linked to the particular microenvironment in which the stem cell resides at the time of isolation. Thus, the utility of common markers that are used to identify stem cells can vary with the site from which they are collected.

Our approach has been to identify markers of critical stem cell functions. Since self renewal is the quintessential stem cell property, we have focused our efforts on renewal pathways. We have identified multiple genes that are highly expressed by normal HSCs, leukemia stem cells that originated from progenitor cells, and human epithelial cancer stem cells, but not by non-self renewing cells in each respective tissue. This genomics analysis described in the preliminary results identified a number of genes that had previously been linked to stem cell self renewal. Similarly, we identified candidate microRNAs that are differentially expressed by breast cancer stem cells and non-tumorigenic cancer cells. Evidence demonstrates that several of these genes and microRNAs have critical stem cell functions and that the function of these genes is also critical to hESC and iPSC self-renewal and maintenance.

To produce a device capable of measuring the frequency of cancer stem cells in a tumor cell population, it is desirable to optimize the gene list used to identify cancer stem cells. As shown in FIG. 1B, we have made great progress in doing so, identifying telomerase as a cancer stem cell marker as well as several genes linked to the process of self renewal. The telomerase component TERT is only expressed in colon cancer cells with an immature phenotype. Moreover, TERT is not efficiently-downregulated with differentiation of some hESC and iPSC lines.

Both normal and cancerous colon epithelial cells are analyzed for the expression of genes linked to crypt cell maturation and self renewal. The self renewal gene list is expanded beyond TERT to maximize confidence that a cell is a stem cell. The expression of genes identified in our analysis of normal and cancer stem cell are measured. Because cancer stem cells can potentially arise from either a stem cell that has escaped the constraints on expansion or progenitor cells that have escaped the counting mechanisms that limit the number of mitoses that they can undergo, the candidate genes are those that are expressed by normal murine HSCs, murine leukemia stem cells that were derived from a progenitor cell, and human breast cancer stem cells. The top candidate genes identified in this list, all of which have been linked to stem cell maintenance, include BMI1, -IDI, IGFBP3, the HOX family members HOXA3, HOXA5, MEIS1, ETS1, ETS2, RUNX2 and STAT3. We will validate which of these genes are linked to cancer stem cell self renewal. To do this, we will systematically test our candidate genes for a role in self renewal of cancer stem cells using in vitro and in vivo techniques.

The expression of genes that regulate self renewal are linked to the expression of genes specific to epithelial cells, including maturation markers, such as keratins and intestinal mucins. This will enable ascertaining that a cell in the analysis is not a normal cell contaminant in the biopsy. Mutations of tumor suppressor genes whose expression is downregulated by the self renewal gene BMI I enable early progenitor cells to self renew. These genes are frequently mutated in colon cancer, thus self renewing colon cancer stem cells will arise from both normal stem cells and early colon progenitor cells. Furthermore, oncogenic mutations will alter gene expression by colon cancer cells. Thus, there may be differences in expression of at least some genes linked to early crypt cell maturation between normal colon epithelial stem cells and their malignant counterpart that will make it possible to distinguish these 2 self renewing cell populations from each other.

We identified 37 miRNAS that were differentially expressed in cancer stem cells and non-tumorigenic cancer cells. Several miRNA clusters were down-regulated in normal tissue stem cells but not in cancer stem cells; moreover, the expression of some miRNAs, such as miR-200c and miR-183 suppressed growth of embryonal carcinoma cells in vitro, abolished their tumor-forming ability in vivo, and inhibited the clonogenicity of breast cancer cells in vitro. These miRNAs, and the other clusters we identified, provide a molecular link that connects breast cancer stem cells and normal stem cell biology. The expression of these microRNAs; which were consistently up-regulated or down-regulated in tumorigenic cells, are probed in single cells from undifferentiated and differentiated hESCs and iPSCs. Essentially, undifferentiated cells are sorted by cell surface markers distinct to pluripotent stem cells such as Tra and SSEA subtypes and assessed for miRNA expression, replating efficiency and population parameters in vivo (outcome of teratoma assays in terms of embryonal carcinoma, mixed embryonic carcinoma/differentiated cell index (% EC vs differentiated), and differentiated cells). Differentiated stem cell populations are obtained by production of embryoid bodies and sorted via positive and negative selection for SSENTRA markers, after 28 days differentiation. We will examine single cells within the sorted populations for: 1) microRNA profiles indicative of cancer stem cells 2) gene expression profile (below), and 3) outcome of transplantation/teratoma assays. We expect that cells "resistant to differentiation" in these populations will form malignant embryonal carcinoma derivatives and co-express markers of differentiated and undifferentiated cells within single cells.

Example 7

Gene Expression Profile at the Single Cell Level

Figure 6:
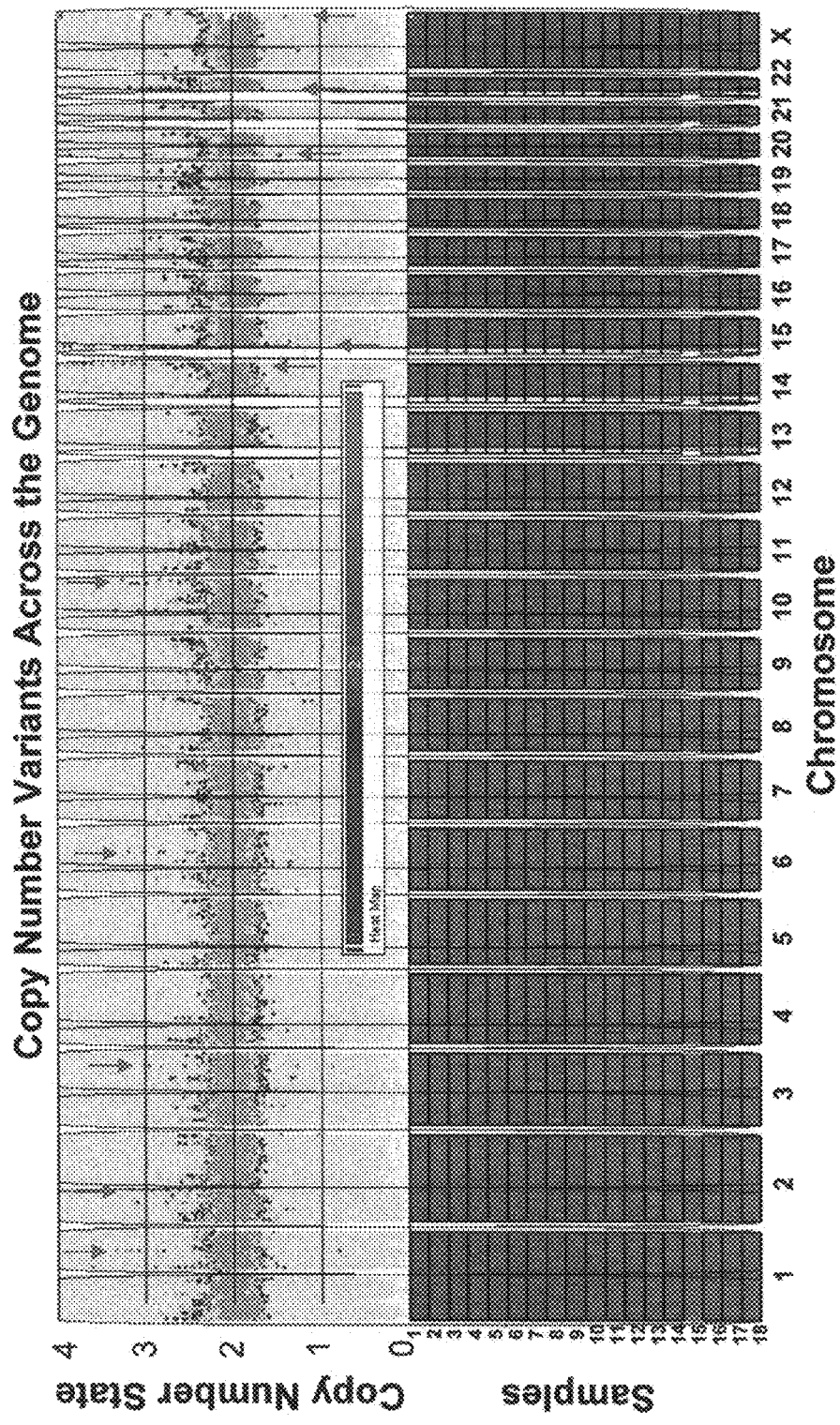
FIG. 6. Copy number variant analysis of 18 cell samples for several thousand CNVs. Several may be associated with genomic instability and give rise to altered pluripotent stem cell properties.

In populations of pluripotent cells, even after differentiation for 21 days, we observe lines that fail to downregulate key markers of tumorigenicity such as TERT (see FIG. 6). In addition, we have observed that approximately 50% of our iPSC lines fail to downregulate both exogenous and endogenous pluripotency markers, in the differentiated state. Essentially, this suggests a "molecular war" between differentiation and self-renewal that we may predict an outcome of proclivity to tumorigenesis. We will optimize the gene list for identification of malignant cells in hESC and iPSC cell cultures by: 1) assaying genes overexpressed in EC (embryonal carcinoma) cells relative to undifferentiated hESCs and IPSCs, and human embryonic blastomeres, 2) cross-referencing the list of genes to include those from Aim 1 (for identification of cancer stem cells), and 3) adding genes of differentiated somatic and germ cell lineages (the later remain in pluripotent stem cells resistant to differentiation). We will then use immune deficient mouse assays to assess tumorigenic potential of subpopulations diagnosed according to malignant potential based on basal gene expression of single cells.

CNV analysis. Chromosomal variants are linked to instability in pluripotent human stem cell populations, with chromosome loss and gain frequently observed. However, few studies have addressed finer structure, high-throughput methods to assess copy number at multiple loci. We propose to adapt our technology for assessment of genome-wide CNV number in independently-derived pluripotent stem cell lines; changes in CNVs will reflect subchromosomal instability. Initially, we can design specific probe sets for addition to our gene/loci list that recognize duplications across the genome, including those previously observed in our laboratory (FIG. 6). The SCAD can accommodate analysis of up to 1000 markers, in its initial design. CNV assays are commercially available and can be correlated with genomic instability in hESCsIiPSCs.

Example 8

Engineering an Automated Device to Identify and Quantify Cancer Stem Cells

An automated device is designed to identify cancer stem cells and calculate their frequency in tumors based on a combination of cell surface phenotype and gene expression. Using the optimized marker/genetic analysis described herein, a similar strategy is used to identify cells with malignant potentia, based on co-expression of markers of the differentiated and undifferentiated state in single cells. This device will make a single cell suspension of embryoid bodies or needle biopsies of a tumor, isolate the cell subpopulations (epithelial, differentiated, undifferentiated) and then do a qRT-PCR of hundreds or thousands of single cells and measure the stem cell content of a tumor or pluripotent cell culture. Such a fully automated device will eliminate the labor-intensive steps currently needed for flow-cytometry sorting of cancer stem cells, and allow a truly hands-off, bed-side diagnostic tool that will need less than 100,000 cells to isolate enough cancer cells for PCR assays to quantify cancer stem cells. Automated operation, effectiveness and low cost associated with microfluidic chip technology will make individualized, rapid genetic diagnosis possible.

At the heart of this system is a microfluidic cell sorter. This device isolates live cells (epithelial cells or cultured pluripotent cells or their products) from the debris (necrotic cells and other particles), sort out the cells from the single cell suspension using fluorescent signals from up to five different surface markers, and places them in individual bins for subsequent genetic studies. Other upstream steps such as digesting the tumor or cell culture to obtain a cell suspension and staining the cells with fluorescent surface markers may be incorporated in this system. How the system is used for tumor analysis is illustrated here: Once the biopsy is obtained, the physician will place the sample in the input port of this system. Utilizing a user friendly computer interface, the physician will set the necessary parameters in the sorting and genetic analysis such as the number and type of surface markers, the number of PCR cycles needed etc, and the machine will perform the rest of the steps without human intervention. Based on previously demonstrated technologies, the system will allow a sorting throughput of at least 30 cells/second.

Figure 7:
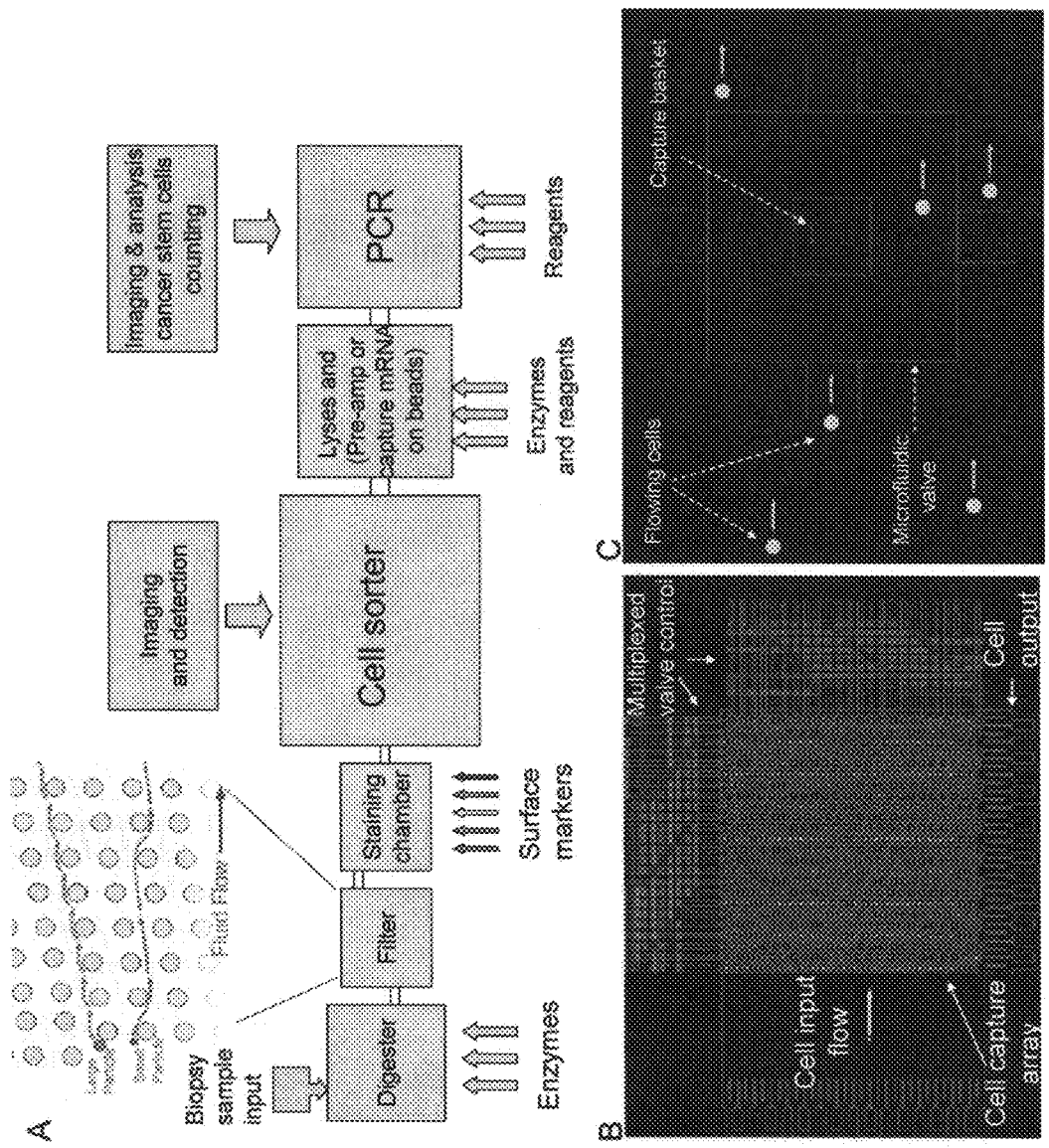
FIG. 7. Single Cell Analysis device, principle.

A single cell analysis device (SCAD) can be modular (FIG. 7) and will perform the following steps in an integrated, fully automated fashion: 1) Digestion of the tissue: The tissue is placed in the input port of the device. Appropriate enzymes are introduced in the device and flowed to perform the digestion of the extracellular matrix in order to obtain a cell suspension. 2) Separation of live cells from the debris: The suspension typically contains live cell with an average size of 10 to 15 micrometers, and debris material with an average size around 5 micrometers. The amount of dead material is sometimes relatively high compared to live cells, therefore it is critical to filter out the dead material for efficient isolation of cells. We accomplish this by flowing the digested tissue suspension through a microfluidic "metamaterial," which allows splitting the fluidic flow according to the size of the particles. 3) Staining: The filtered single cell suspension is stained using appropriate surface markers in a different compartment of the microfluidic device. Staining with up to five different markers may be useful in obtaining a high purity population of cancer cells. 4) Sorting: The stained single-cell suspension is flowed into the next compartment of the microfluidic device to sort out the cancer cells from the rest of the cells. Poisson statistics and the Monte Carlo simulations indicate that only 2,000-20,000 cancer cells need to be sorted in order to be able to detect two-fold changes in the cancer stem cells, within a confidence level of 99%. Such a small number of cells currently cannot be sorted efficiently using flow-cytometry, as the initial sample size needed for FACS is around one million cells. We will achieve this using microfluidic based sorting for cycling of the cell suspension indefinitely in an air-tight, isolated small volume environment that will not waste cells.

Flow based microfluidic cell sorter: A microfluidic cell sorter with a throughput of nearly 50 cells/second has been demonstrated, where cells were flowed at high speed through a laser beam (see Di Carlo et al. Lab Chip 2006; 6:1445-1449), and the scattered light was detected and analyzed. Faster electronics and more efficient imaging equipment allow an improvement of the throughput by an order of magnitude, which will bring down the sorting time to less than ten minutes.

Parallel sorting: a cell sorter is being developed based on capturing the cells on a dense, 2-D array of microfluidic chambers that can be individually addressed (FIGS. 7B and 7C above). The cells are flowed into the sorter array and are captured by microfabricated baskets. Such baskets were previously demonstrated to have more than 50% single cell capture efficiency in a freely flowing suspension (Di carlo et al., supra). After all the baskets are filled, the microfluidic valves are closed, and the array is imaged using custom designed, computer controlled optics in all 5 fluorescent colors needed to identify tumorigenic cells. This new chip also allows phase contrast imaging, which may prove useful to study cell morphology. The identified tumorigenic cells are flowed into the next module for lysis, while the rest of the cells are flowed out of the chip. This new cell sorter allows working with extremely small initial number of cells, as the cells can be cycled many times and therefore will not be wasted. Current microfluidic chip technology allows us to place nearly 10,000 of these elements on a 3×3 cm area, which can be rapidly interrogated (single shot) using state-of-the art imagers, such as the one used by Fluidigm Biomark system. This cell sorter will have a throughput of nearly 30 cells/second. One advantage of using the parallel sorting device as opposed to the flow based cell sorter is that imaging during sorting and PCR can be performed by the same imager, thus allowing us to relate fluorescence and morphology data to genetic data of individual cells.

Cell lysis and mRNA capture: Sorted cancer stem cells are flowed into the next module for lysis in individual chambers. mRNA may be captured on a column of oligo-dT beads, reverse transcribed on the beads as already demonstrated (Marcus et al. Anal Chem 2006; 78:3084-3089) and processed off chip via a new gene sequencing protocol developed for the Heliscope, or may be transferred to a macroscopic well (micro-liter range) and mixed with: reagents to preamplify a set of genes following current protocols. Preamplified samples are transferred to a module similar to the Fluidigm Dynamic array chip for qRT-PCR and determination of true cancer stem cell content.

Based on an analysis of normal breast and blood stem cells as well as colon, head and neck, and breast cancer stem cells, we have identified a novel single cell assay that for the first time makes it possible to accurately and unequivocally identify and count cancer stem cells in biopsy specimens and cultured pluripotent stem cell populations. As a proof of principle, we applied this assay to an analysis of single colon cancer cells. To do this, we used FACS to sort $CD66^+CD44$ lineage colon cancer cells from early passage xenografts established from 2 different patients. These markers allow an approximately 3-5 fold enrichment of colon cancer stem cells (CoCSCs) in a tumor. We had suspected that cancer cells isolated with these markers were only partially enriched for CoCSCs. The single cell gene expression analyses and subsequent tumorigenicity studies demonstrate that indeed $CD66^+CD44^+$Lineage-cells are a mixture of CoCSCs and non-tumorigenic cells and that this assay can be used to more accurately identify the frequency of CoCSCs in a biopsy specimen. The single cell analysis reveals a hierarchical developmental structure of colon cancer cells that is reminiscent of a normal colon crypt. Notably, we find that the most immature cells in the colon tumor express TERT, a component of the telomerase complex that is critical for long term maintenance of a tumor. Expression of LGR5, which marks normal colon stem cells, is also limited to immature cells. By contrast, genes expressed by maturing colon crypt cells including MUC2, 'CK20, CA-2, and especially CD66a were expressed by cells that do not co-express immature cell markers, most notably TERT. This suggests that these cells, like normal maturing epithelial crypt cells, have limitations on their ability to undergo extensive mitoses. Indeed, we have transplanted $CD66a^+$ (differentiated colon cancer cells) and CD66a'" colon cancer cells into immunodeficient mice. CD66a' cells formed tumors (5 of 6 injections) while $CD66^+$ cells did not (0 of 5 injections). Similarly, in 2 human breast cancer tumors that were tested the CD66ew cells were enriched for cancer stem cells when tested in the immunodeficient mouse model. These results demonstrate that single cell gene expression analysis enables identification and quantitation of cancer stem cells in biopsies and cultures.

Example 9

Figure 8:
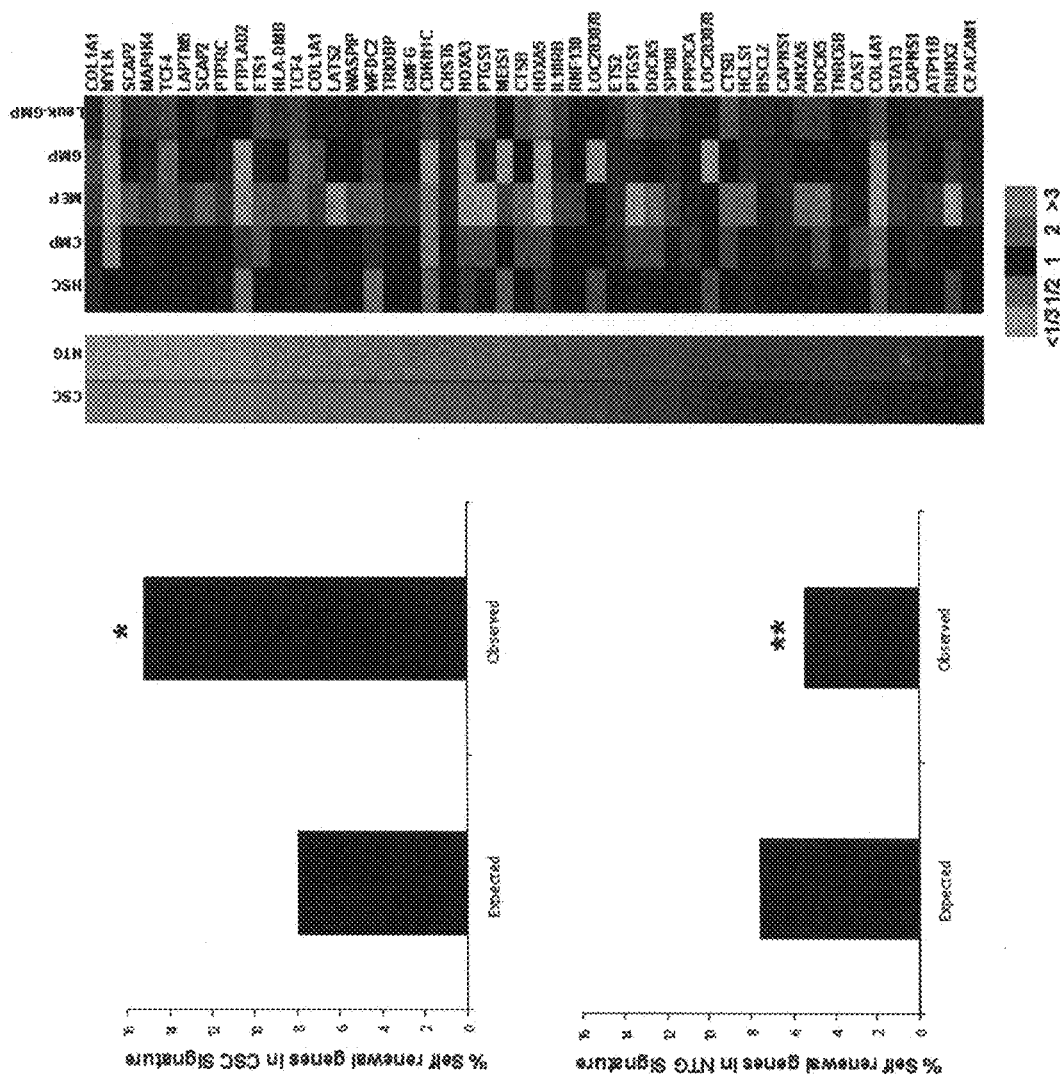
FIG. 8. Gene Set Enrichment analysis of the expression of stem-cell linked genes. Genes expressed by self renewing normal HSCs, leukemia stem cells derived from Granulocyte/Macrophage progenitors (GMPs) but not by non-self renewing normal GMPs were analyzed in breast cancer stem cells (CSC) and their non-tumorigenic progeny (NTG). As predicted, these genes were significantly overrepresented in the CSCs gene expression signature. A heat map of overexpressed genes is shown.

A Gene Expression Signature Shared by Normal Stem Cells and Cancer Stem Cells, in Both Blood and Mammary Epithelial Tissues It has become apparent in recent years that cancer stem cells can arise from different cell compartments. Some likely arise from a mutant stem cell that has lost the constraints on: expansion of the stem cell pool. Others arise from a more differentiated early progenitor cell that has lost the counting mechanism that normally restricts the number of mitoses that they can undergo. Of course, many of the markers of cancer or leukemia stem cells that arise from a stem cell or a progenitor cell are different. Regardless of the cell of origin, however, the stem cells will retain the ability to self renew. We reasoned that it is likely that some of the pathways that regulate self renewal in cancer stem cells arising from either the stem cell compartment or a partially differentiated progeny are shared with each other and with normal HSCs. To test this hypothesis, we analyzed whether genes expressed by normal mouse HSCs and murine leukemia stem cells arising from progenitor cells (i.e. self renewing populations) but not normal progenitor cells (i.e. non-self renewing population) are also expressed by human breast cancer stem cells but not their non-tumorigenic counterparts. Remarkably, the human cancer stem cells, but not their non-tumorigenic counterparts, overexpress these genes (FIG. 8). We have also generated 2 other gene lists to identify other potential candidates: i) genes expressed by breast cancer stem cells and normal breast stem cells, but not by non-tumorigenic cancer cells or mature breast epithelial progenitor cells, ii) genes expressed by normal human HSCs and human breast cancer stem cells but not human blood progenitor cells or non-tumorigenic breast cells.

Many of these genes have been linked to self renewal and cancer. These include the insulin growth factor binding partner IGFBP3, the HOX family members HOXA3, HOXA5, ME1S1 as well as transcription factors like ETS1, ETS2, RUNX2 and STAT3. It was tested whether the transcription factor STAT3 is a bona fide cancer stem cell regulator. STAT3 plays a role in the maintenance of both ES cells and HSCs. The genomics analysis of both mouse and human breast cancer stem cells revealed that many STAT3 activated transcripts were overexpressed by the cancer stem cells. Next, when we examined immunochemistry analysis of breast tumors the STAT3 positive cells tended to be concentrated on the invasive edge of the cancer and the protein was not seen in the more differentiated-looking cells in the interior parts of tumors. Finally, there are small molecule inhibitors of STAT3. Such inhibitors can be tested in cancer stem cell models. The effect of the STAT3 inhibitor cucurbitacin on the clonogenic ability of murine breast cancer stem cells was tested. A short, 24 hour exposure to the inhibitor reduced the number of colonies by ~50% (p<0.02, t test). These results suggest that STAT3 plays a critical role in at least some breast cancer stem cells.

A second gene of interest is MEIS1. MEIS1 is preferentially expressed by normal blood and breast stem cells, leukemia stem cells, and breast cancer stem cells. Genetic studies have shown that expression of MEIS1 is absolutely required for the self renewal and maintenance of both normal blood stem cells and their leukemic counterparts. MEIS1 may regulate breast cancer stem cell renewal.

Particularly interesting candidate genes expressed by both normal and cancer stem cells include CAV1, GAS1, MAP4K4 (kinase) MYLK (kinase), PTK2 (kinase), DAPK1 (kinase), LATS (kinase), FOSL2, AKT3 (kinase), PTPRC (tyrosine phosphatase), MAFF (oncogene), RRAS2 (related to RAS), NFKB, ROBO1, IL6ST (activates STAT3), CR1M1, PLS3, SOX2, CXCL14, ETS1, ETS2, MEIS1 and STAT3, as well as CD47. Interesting candidate genes overexpressed by cancer stem cells but not normal stem cells include RGS4, CAV2, MAF (oncogene) WT1 (oncogene), SNAI2, FGFR2, MEIS2, 101, 103, ID4 and FOXC1.

Example 10

Whole Transcriptome Analysis of Hematopoietic Stem Cells

Figure 9:
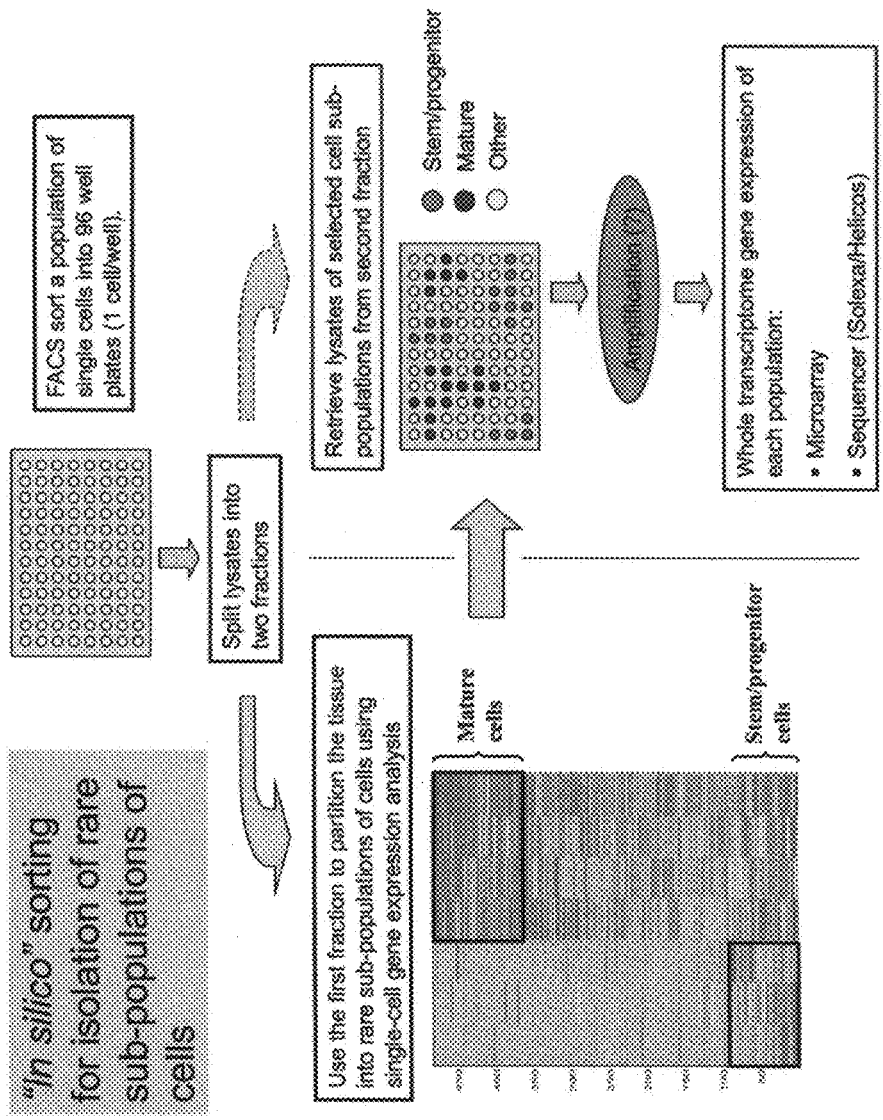
FIG. 9. A schematic of "in silico" sorting for isolation of rare sub-populations of cells. Cell populations, such as hematopoietic stem cells, are sorted by FACS into 96-well plates, containing a single cell. Cells are lysed and the lysate is divided into two fractions. One fraction of the lysate is analyzed for expression of a set of genes, allowing the cells to be characterized on the basis of transcription, rather than surface-protein expression. Utilizing this information, selected lysates and/or lysates pooled from like cells are subjected to whole-transcriptome analysis.

In this example we seek to use transcriptome analysis of hematopoietic stem cells. A general outline of this embodiment is shown in FIG. 9. In the present example a population of cells suspected of comprising hematopoietic stem cells is isolated from a test subject. Cells are then prepared for FACS analysis by exposing the cell population to fluorescent antibodies to known hematopoietic stem markers (e.g., CD34, Thy1, etc.). Cells are sorted into 96-well plates, such that each well contains no more than a single cell.

Isolated single cells are lysed and the lysates are divided into two portions. The first portion is subjected to single-cell gene expression analysis by real-time PCR, essentially as described in Example 1, using a selection of genes which allow for distinguishing between HSCs and non-HSCs, either by level or presence of expression (e.g., CD34+, CD19−; CD17−). After identifying HSCs within the population lysates from the single cells identified as being HSCs are pooled. A cDNA library is created by amplifying total mRNA using standard methods. The cDNA is then sequenced using a "next generation" method such as any of those described herein. The sequenced transcriptome is then analyzed to determine whether unique genes and/or surface markers are present.

Following identification of a surface marker unique to HSCs, antibodies which specifically bind to the surface markers are prepared by commercially available techniques. The specificity and effectiveness of the antibodies are confirmed (e.g., binding to isolated and/or recombinant protein). The antibodies are then labeled with a fluorescent moiety. FACS sorting and/or analysis can then be performed on other populations of cells (e.g., from the same or different subjects) using the antibodies to the newly discovered surface antigens.

Example 11

Analysis of Therapeutic Agents

In this example, selection of candidate therapeutic agents is performed. Target cells, e.g., colon cancer stem cells and colon cancer cells (differentiated) are isolated and analyzed at the single cell level as described above. Target cells are separated from a biopsy specimen using markers specific for the target cells (e.g., FACS separation using target-cell-specific antibodies and/or fluorescent labeling of target-cell specific nucleic acids) previously identified.

Target cells are separated into addressable positions comprising a single cell. The isolated cells are then exposed to a library of candidate therapeutic agents (e.g., antibodies, toxin-conjugated antibodies, small molecules). Cells are then collected and analyzed for gene expression patterns and/or cell viability. Successful candidate therapeutic agents can be those which target the cells for death. Alternately, candidate therapeutic agents can alter expression of genes known to be mis-regulated (e.g., up- or down-regulated) compared to expression patterns from non-disease state cells. Exposure of a target cell to a candidate therapeutic agent can result in alteration of nucleic acid expression pattern(s) which more closely resemble the pattern(s) of normal (i.e., non-disease-state) cells. Candidate therapeutic agents which show promise in killing or altering target cells are then exposed to normal cells to determine their potential use as a therapeutic agent (e.g., if the candidate agent kills target cells and normal cells, it can be excluded as a possibly useful agent).

What is claimed is:

1. A method of identifying different cell populations in a heterogeneous cell sample, comprising:
   randomly partitioning individual cells from said heterogeneous cell sample into discrete locations on a cell capture array with wells just large enough to fit a single cell;
   identifying certain individually partitioned cells in the discrete locations on the cell capture array using one or more surface markers;
   sorting the certain individually partitioned cells from the discrete locations using a microfluidic device;
   performing transcriptome analysis on a plurality of genes of the individually sorted cells from the discrete locations; and
   performing clustering analysis to identify different cell populations.

2. The method of claim 1, wherein said individual cells are not enriched prior to said partitioning.

3. The method of claim 1, wherein said transcriptome analysis is performed on at least 1000 individual cells in parallel.

4. The method of claim 1, wherein said transcriptome analysis is performed using nucleic acid analysis.

5. The method of claim 1, wherein said discrete locations are on a microarray.

6. The method of claim 1, wherein said transcriptome analysis comprises analyzing expressed RNA, non-expressed RNA, or both.

7. The method of claim 1, wherein said transcriptome analysis is whole transcriptome analysis.

8. The method of claim 1, wherein said transcriptome analysis comprises amplifying RNA using a set of at least five primer pairs.

9. The method of claim 8, wherein said at least five primer pairs are not nested primers.

10. The method of claim 1, wherein said transcriptome analysis is performed in parallel or substantially in real time on said individually sorted cells.

11. The method of claim 1, wherein said different cell populations are non-cancerous stem cells, non-cancerous progenitor cells, non-cancerous mature cells, inflammatory cells, cancer cells, cancer stem cells or non-tumorigenic cancer stem cells.

* * * * *